US010793597B2

(12) United States Patent
Wilson

(10) Patent No.: US 10,793,597 B2
(45) Date of Patent: Oct. 6, 2020

(54) **METHODS FOR THE TREATMENT OF MITOCHONDRIAL DISEASES ASSOCIATED WITH A MUTATION IN *SURF 1* OR *POLG* GENE RESULTING IN A DISRUPTION OF MITOCHONDRIAL OXIDATIVE PHOSPHORYLATION**

(71) Applicant: STEALTH BIOTHERAPEUTICS CORP, Monaco (MC)

(72) Inventor: D. Travis Wilson, Newton, MA (US)

(73) Assignee: STEALTH BIOTHERAPEUTICS CORP, Monaco (MC)

(*) Notice: Subject to any disclaimer, the term of this patent is extended or adjusted under 35 U.S.C. 154(b) by 0 days.

(21) Appl. No.: 14/771,411

(22) PCT Filed: Feb. 28, 2014

(86) PCT No.: PCT/US2014/019645
§ 371 (c)(1),
(2) Date: Aug. 28, 2015

(87) PCT Pub. No.: WO2014/134562
PCT Pub. Date: Sep. 4, 2014

(65) Prior Publication Data
US 2016/0002293 A1 Jan. 7, 2016

Related U.S. Application Data

(60) Provisional application No. 61/771,642, filed on Mar. 1, 2013, provisional application No. 61/771,534, filed on Mar. 1, 2013.

(51) Int. Cl.
| | | |
|---|---|---|
| *A61K 38/00* | (2006.01) | |
| *A61K 49/00* | (2006.01) | |
| *A61K 38/18* | (2006.01) | |
| *C07K 14/475* | (2006.01) | |
| *C07K 14/48* | (2006.01) | |
| *A61B 5/00* | (2006.01) | |
| *C07K 5/11* | (2006.01) | |
| *A61K 38/07* | (2006.01) | |
| *C07K 5/107* | (2006.01) | |
| *A61K 45/06* | (2006.01) | |
| *A61K 9/127* | (2006.01) | |
| *C07K 5/10* | (2006.01) | |
| *A61L 29/16* | (2006.01) | |
| *C07K 5/09* | (2006.01) | |
| *A61K 9/00* | (2006.01) | |

(Continued)

(52) U.S. Cl.
CPC ............ *C07K 5/1019* (2013.01); *A61K 38/07* (2013.01); *C07K 5/1016* (2013.01); *A61K 9/0048* (2013.01); *A61K 9/0051* (2013.01); *A61K 9/127* (2013.01); *A61K 9/5031* (2013.01); *A61K 9/5052* (2013.01); *A61K 38/00* (2013.01); *A61K 38/03* (2013.01); *A61K 38/06* (2013.01); *A61K 38/08* (2013.01); *A61K 45/06* (2013.01); *A61K 2300/00* (2013.01); *A61L 29/16* (2013.01); *A61L 2300/40* (2013.01); *A61Q 19/08* (2013.01); *C07K 5/06086* (2013.01); *C07K 5/0812* (2013.01); *C07K 5/0817* (2013.01); *C07K 5/10* (2013.01); *C07K 5/101* (2013.01); *C07K 5/1008* (2013.01); *C07K 5/1024* (2013.01); *C07K 14/705* (2013.01); *G01N 2800/207* (2013.01); *G01N 2800/52* (2013.01)

(58) Field of Classification Search
CPC .... A61K 2300/00; A61K 38/00; A61K 38/04; A61K 38/07; A61K 31/00; A61K 38/03; A61K 38/06; A61K 8/64; A61K 38/08; A61K 45/06; A61K 9/0048; A61K 9/0051; A61K 9/5031; A61K 9/5052; C07K 5/1019; C07K 5/1016; C07K 14/705; C07K 5/1008; C07K 5/101; C07K 5/1024; C07K 5/06086; C07K 5/0812; C07K 5/10; A61L 2300/40; A61L 29/16; A61L 31/16; G01N 2800/2007; G01N 2800/52
See application file for complete search history.

(56) References Cited

U.S. PATENT DOCUMENTS

| | | | |
|---|---|---|---|
| 4,522,811 A | 6/1985 | Eppstein et al. | |
| 5,674,534 A | 10/1997 | Zale et al. | |

(Continued)

FOREIGN PATENT DOCUMENTS

| | | |
|---|---|---|
| JP | 2013-521231 | 6/2013 |
| WO | WO-96/40073 | 12/1996 |

(Continued)

OTHER PUBLICATIONS

Zhao et al. JBC. 2004; 33: 34682-34690.*

(Continued)

*Primary Examiner* — Chang-Yu Wang
(74) *Attorney, Agent, or Firm* — Foley & Lardner LLP

(57) ABSTRACT

The disclosure provides methods of preventing, ameliorating or treating disruption of mitochondrial function and symptoms thereof. The methods provide administering aromatic-cationic peptides in effective amounts to prevent, treat or ameliorate the disruption of mitochondrial oxidative phosphorylation in a cell such as that found in a subject suffering from, or predisposed to a mitochondrial disease or disorder. In some embodiments, the methods comprise administering to a subject suffering from, or at risk for a mitochondrial disease or disorder, an effective amount of an aromatic-cationic peptide to subjects in need thereof.

6 Claims, 18 Drawing Sheets
Specification includes a Sequence Listing.

(51) Int. Cl.

| | | |
|---|---|---|
| A61K 9/50 | (2006.01) | |
| A61K 38/06 | (2006.01) | |
| A61Q 19/08 | (2006.01) | |
| A61K 38/08 | (2019.01) | |
| C07K 14/705 | (2006.01) | |
| A61K 38/03 | (2006.01) | |
| C07K 5/103 | (2006.01) | |
| C07K 5/117 | (2006.01) | |
| C07K 5/087 | (2006.01) | |
| C07K 5/068 | (2006.01) | |

(56) References Cited

U.S. PATENT DOCUMENTS

| | | | | |
|---|---|---|---|---|
| 5,716,644 | A | 2/1998 | Zale et al. | |
| 6,468,798 | B1 | 10/2002 | Debs et al. | |
| 7,550,439 | B2 * | 6/2009 | Szeto | A61K 38/07 514/1.1 |
| 7,576,061 | B2 * | 8/2009 | Szeto | A61K 38/03 514/1.1 |
| 7,718,620 | B2 * | 5/2010 | Szeto | A61K 38/03 514/15.1 |
| 7,781,405 | B2 * | 8/2010 | Szeto | A61K 38/07 514/1.4 |
| 8,143,219 | B2 * | 3/2012 | Szeto | A61K 38/06 514/15.4 |
| 8,404,646 | B2 * | 3/2013 | Schiller | A61K 38/03 514/21.3 |
| 8,592,373 | B2 * | 11/2013 | Szeto | A61K 38/06 514/15.4 |
| 8,618,061 | B2 * | 12/2013 | Szeto | A61K 38/07 514/17.7 |
| 8,940,696 | B2 * | 1/2015 | Szeto | A61K 38/06 514/15.4 |
| 8,957,030 | B2 * | 2/2015 | Szeto | A61K 38/03 514/1.1 |
| 9,241,933 | B2 * | 1/2016 | Cohen | A61K 45/06 |
| 9,457,057 | B2 * | 10/2016 | Tompkins | A61K 38/07 |
| 10,047,395 | B2 | 8/2018 | Wilson | |
| 2004/0248808 | A1 * | 12/2004 | Szeto | A61K 38/03 514/15.1 |
| 2006/0084606 | A1 * | 4/2006 | Szeto | A61K 38/07 514/1.4 |
| 2006/0251641 | A1 | 11/2006 | Keimel | |
| 2007/0015711 | A1 * | 1/2007 | Szeto | A61K 38/07 514/1.4 |
| 2007/0026090 | A1 * | 2/2007 | Tirosh | A61K 31/095 424/702 |
| 2007/0027087 | A1 * | 2/2007 | Szeto | A61K 38/03 514/15.1 |
| 2007/0135335 | A1 | 6/2007 | Collier et al. | |
| 2007/0265216 | A1 | 11/2007 | Gross et al. | |
| 2008/0318909 | A1 | 12/2008 | Sparagna et al. | |
| 2009/0143279 | A1 | 6/2009 | Mootha et al. | |
| 2009/0221514 | A1 * | 9/2009 | Szeto | A61K 38/06 514/1.1 |
| 2009/0298848 | A1 | 12/2009 | Stewart | |
| 2009/0305319 | A1 | 12/2009 | Baudenbacher et al. | |
| 2010/0158995 | A1 | 6/2010 | Mill et al. | |
| 2010/0190718 | A1 * | 7/2010 | Schiller | A61K 38/03 514/1.1 |
| 2010/0311664 | A1 * | 12/2010 | Szeto | A61K 38/07 514/17.7 |
| 2010/0331265 | A1 * | 12/2010 | Tompkins | A61K 38/07 514/21.9 |
| 2011/0008310 | A1 * | 1/2011 | Cataldo | A01K 67/0271 424/94.4 |
| 2011/0039766 | A1 | 2/2011 | Szeto | |
| 2011/0082084 | A1 | 4/2011 | Szeto et al. | |
| 2011/0136725 | A1 | 6/2011 | Dong | |
| 2011/0172312 | A1 | 7/2011 | Miller et al. | |
| 2011/0197294 | A1 | 8/2011 | Gottlieb et al. | |
| 2012/0021970 | A1 * | 1/2012 | Schiller | A61K 38/03 514/1.2 |
| 2012/0046363 | A1 | 2/2012 | Stanley | |
| 2012/0122957 | A1 * | 5/2012 | Dillin | A61K 31/713 514/44 A |
| 2013/0017150 | A1 * | 1/2013 | Szeto | A61K 38/06 424/1.85 |
| 2013/0040901 | A1 | 2/2013 | Szeto et al. | |
| 2013/0244957 | A1 * | 9/2013 | Szeto | A61K 38/03 514/21.9 |
| 2013/0288985 | A1 * | 10/2013 | Jurkunas | A61K 9/0048 514/20.8 |
| 2013/0345312 | A1 * | 12/2013 | Jankowski | A61K 31/122 514/682 |
| 2014/0031432 | A1 * | 1/2014 | Jankowski | A61K 31/122 514/681 |
| 2014/0107033 | A1 * | 4/2014 | Szeto | A61K 38/06 514/15.4 |
| 2014/0288012 | A1 * | 9/2014 | Tompkins | A61K 38/07 514/21.9 |
| 2014/0342004 | A1 | 11/2014 | Aprikyan et al. | |
| 2014/0349941 | A1 * | 11/2014 | Wilson | A61K 38/04 514/15.4 |
| 2014/0349942 | A1 * | 11/2014 | Szeto | A61K 38/07 514/17.7 |
| 2014/0378396 | A1 * | 12/2014 | Wilson | A61K 38/04 514/21.9 |
| 2015/0010588 | A1 * | 1/2015 | Szeto | C07K 5/1019 424/185.1 |
| 2015/0018288 | A1 * | 1/2015 | Wilson | A61K 9/0051 514/20.8 |
| 2015/0246092 | A1 | 9/2015 | Wilson et al. | |
| 2015/0266946 | A1 * | 9/2015 | Sinclair | A61K 38/1709 424/135.1 |
| 2015/0353602 | A1 * | 12/2015 | Szeto | A61K 38/06 514/15.4 |
| 2015/0359838 | A1 * | 12/2015 | Szeto | A61K 38/03 514/21.9 |
| 2016/0175380 | A1 * | 6/2016 | Jurkunas | A61K 9/0048 424/450 |
| 2016/0194708 | A1 | 7/2016 | Wilson | |
| 2016/0228487 | A1 | 8/2016 | Wilson et al. | |
| 2016/0361377 | A1 * | 12/2016 | Wilson | A61K 9/0051 |

FOREIGN PATENT DOCUMENTS

| | | |
|---|---|---|
| WO | WO-99/15154 | 4/1999 |
| WO | WO-00/38651 | 7/2000 |
| WO | WO-2004/070054 A3 | 4/2005 |
| WO | WO-2005/072295 A2 | 8/2005 |
| WO | WO-2006/122140 | 11/2006 |
| WO | WO-2010/120431 | 10/2010 |
| WO | WO-2011/082084 A2 | 7/2011 |
| WO | WO-2011/082324 A1 | 7/2011 |
| WO | WO-2011/096398 | 8/2011 |
| WO | WO-2011/106717 | 9/2011 |
| WO | WO-2011/116007 A1 | 9/2011 |
| WO | WO-2011/139992 A1 | 11/2011 |
| WO | WO-2012/129427 | 9/2012 |
| WO | WO-2013/049697 | 4/2013 |

OTHER PUBLICATIONS

PUccio et al. Curr. Opin. Genetics Develop. 2002; 12: 272-277.*
The fact sheet of Leigh syndrome, retrieved from the Genetics Home Reference website: https://ghr.hlm.nih.gov/condition/leigh-syndrome published Feb. 21, 2017.*
Ristow et al. PNAS, 2000; 97:12239-12243.*
The fact sheet of Leigh syndrome retrieved from the website of Genetics Home Reference from US National Library of Medicine, ghr.nlm.nih.gov/condition/leigh-syndrome on Mar. 4, 2019.*
Saneto et al. Pediatric Neurol. 2013; 48: 167-178, published online Sep. 2012, dx.doi.org/10.1016/j.pediatrneurol.2012.09.014.*
The fact sheet of Progressive external ophthalmoplegia, retrieved from the website of Genetics Home Reference from US National

(56) References Cited

OTHER PUBLICATIONS

Library of Medicine, ghr.nlm.nih.gov/condition/progressive-external-ophthalmoplegia on Mar. 4, 2019.*
The fact sheet of ataxia neuropathy spectrum, retrieved from the website of Genetics Home Reference from US National Library of Medicine, ghr.nlm.nih.gov/condition/ataxia-neuropathy-spectrum on Mar. 4, 2019.*
Martin et al., Arch Neurol. 2005; 62:659-661.*
Farina et al., Am. J. Neuroradiol. 2002; 23:1095-1100.*
Ferraris et al., Arch. Neurol. 2008; 65:125-131.*
Menezes et al., Dev. Med. & Child Neurol. 2012; 54: 407-414.*
Acín-Pérez, Rebecca et al., "Respiratory Active Mitochondrial Supercomplexes," Molecular Cell, (Nov. 21, 2008), vol. 32, No. 4, pp. 529-539.
Amselem, S., "Liposome Technology," (1993), vol. 1, 2nd Ed. CRC Press, (26 pages).
Ashley, Neil et al., "Depletion of mitochondrial DNA in fibroblast cultures from patients with POLG1 mutations is a consequence of catalytic mutations," Hum. Mol. Gene., (2008), vol. 17, No. 16, pp. 2496-2506.
Blok, M.J. et al., "The unfolding clinical spectrum of POLG mutations," J. Med. Genet., (2009), vol. 46, No. 22, pp. 776-785.
Chonn, Arcadio et al., "Recent Advances in Liposomal Drug-Delivery Systems," Current Opinion in Biotechnology, (1995), vol. 6, pp. 698-708.
Diaz, Francisca et al., Cytochrome c Oxidase Is Required for the Assembly/Stability of Respiratory Complex I in Mouse Fibroblasts, Mol. Cell. Bio., (Jul. 2006), vol. 26, No. 13, pp. 4872-4881.
Gregoriadis, G., "Engineering Liposomes for Drug Delivery: Progress and Problems," Trends in Biotechnology, (Dec. 1995), vol. 13, No. 12, pp. 527-537.
Han, Xianlin et al., "Shotgun lipidomics of cardiolipin molecular species in lipid extracts of biological samples," J Lipd Res, (2006), 47(4), pp. 864-879.
Houtkooper et al., "Cardiolipin and monolysocardiolipin analysis in fibroblasts, lymphocytes, and tissues using high-performance liquid chromatography-mass spectrometry as a diagnostic tests for Barth syndrome," Analytical Biochemistry, (2009), vol. 387, pp. 230-237.
Houtkooper, Riekelt H. et al., "The Enigmatic Role of Tafazzin in Cardiolipin Metabolism," Biochimica et Biophysica Acta 1788, (2009), pp. 2003-2014.
International Search Report and Written Opinion of the International Searching Authority for International Application No. PCT/US14/19622 dated Jun. 3, 2014, 11 pages.
International Search Report and Written Opinion of the International Searching Authority for International Application No. PCT/US14/19645, dated Jun. 17, 2014, 11 pages.
International Search Report and Written Opinion of the International Searching Authority for International Application No. PCT/US14/43711 dated Jan. 2, 2015, 10 pages.
Koshkin, Vasilij et al., "Cardiolipin prevents rate-dependent uncoupling and provides osmotic stability in yeast mitochondria," Biochem. J., (2002), vol. 364, pp. 317-322.
Kozarich, John W. et al., "Next generation therapeutics: Looking to the horizon: Editorial overview," Current Opinion in Chemical Biology, (1998), vol. 2, Issue 4, pp. 439-440.
Lichtenberg, Dov et al., "Liposomes: Preparation, Characterization, and Preservation," Methods Biochem. Anal., (1998), vol. 33, pp. 337-462.
Ma, Lining et al., "The Human TAZ Gene Complements Mitochondrial Dysfunction in the Yeast taz1Δ Mutant: Implications for Barth Syndrome," (2004), vol. 279, No. 43, pp. 44394-44399.
McHugh, John C. et al., "Sensory ataxic neuropathy dysarthria and ophthalmoparesis (SANDO) in a sibling pair with a homozygous p. A467T POLG mutation," Muscle Nerve, (2010), vol. 41, No. 2, pp. 265-269.
Mizuguchi, Hiroyuki et al., "Intratumor administration of fusogenic liposomes containing fragment A of diphtheria toxin suppresses tumor growth," Cancer Lett., (1996), vol. 100, Issue 1, pp. 63-69.

Palsdottir, Hilder et al., "Lipids in membrane protein structures," Biochim Biophys Acta, (Nov. 2004), vol. 1666 (1-2), pp. 2-18.
Reddy, K. Rajender, "Controlled-Release, Pegylation, Liposomal Formulations: New Mechanisms in the Delivery of Injectable Drugs," Ann Pharmacother., (Jul./Aug. 2000), vol. 34, pp. 915-923.
Sabbah, Hani N. et al., "A canine model of chronic heart failure produced by multiple sequential coronary microembolizations," Am J Physiol.-Heart and Circulatory Physiology, (1991), vol. 260, Issue pp. H1379-H1384.
Schlame, Michael et al., "The biosynthesis and functional role of cardiolipin," Prog. Lipid Res., (May 2000), vol. 39, Issue 3, pp. 257-288.
Schulte, Claudia et al., "Ataxia with Ophthalmoplegia or Sensory Neuropathy is Frequently caused by POLG Mutations," Neurology, (Sep. 15, 2009), vol. 73, No. 11, pp. 898-900.
Spinazzola, A. et al., "Clinical and molecular features of mitochondrial DNA depletion syndromes," J. INhert. Metab. Dis., (2009), vol. 32, Issue 2, pp. 143-158.
Stewart, J.D. et al., "Novel POLG1 mutations associated with neuromuscular and liver phenotypes in adults and children," J. Med. Genet., (Mar. 2009), vol. 46, No. 3, pp. 209-214.
Tarnavski, Oleg et al., "Mouse cardiac surgery: comprehensive techniques for the generation of mouse models of human diseases and their application for genomic studies," Physiol. Genomics, (2004), vol. 16, Issue 3, pp. 349-360.
Van Goethem, Gert et al., "Mutation of POLG is associated with progressive external ophthalmoplegia characterized by mtDNA deletions," Nature Genetics, (Jul. 2001), vol. 28, No. 3, pp. 211-212.
Weiner, Alan L., "Liposomes for Protein Delivery: Selecting Manufacture and Development Processes," Immunomethods, (1994), 4(3), pp. 201-209.
Williams, Siôn L. et al., "Cytochrome c Oxidase Subassemblies in Fibroblast Cultures from Patients Carrying Mutations in COX10, SCO1, or SURF1," J. Biol. Chem., (2004), vol. 279, No. 9, pp. 7462-7469.
Wong, Lee-Jun C. et al., "Molecular and Clinical Genetics of Mitochondrial Diseases Due to POLG Mutations," Hum. Mutat., (Sep. 2008), vol. 29, No. 9, pp. E150-E172.
Zhao, Kesheng et al., "Transcellular Transport of a Highly Polar 3+ Net Charge Opioid Tetrapeptide", Journal of Pharmacology and Experimental Therapeutics, (2003), vol. 304, No. 1, pp. 425-432.
Extended Search Report dated EP 14756991.7, dated Jul. 19, 2016.
Extended Search Report issued on EP Application 14757000.6, dated Jul. 16, 2016.
Non-Final Office Action on U.S. Appl. No. 14/771408 dated Aug. 10, 2016.
Schlame et al., "Barth syndrome, a human disorder of cardiolipin metabolism," FEBS Letters 580, pp. 5450-5455, 2006.
Takeda et al., "Barth syndrome diagnosed in the subclinical stage of heart failure based on the presence of lipid storage myopathy and isolated noncompaction of the ventricular myocardium," Eur J Pediatr (2011) 170:1481-1484.
Voller, A. et al., "Enzyme immunoassays with special reference to ELISA techniques," J. Clinical Pathology, (1978), vol. 31, Issue 6, pp. 507-520.
Notice of Allowance on U.S. Appl. No. 14/771,408 dated Mar. 1, 2017.
Second Office Action issued on Chinese Application 201480022767.2, dated Nov. 9, 2017.
Non-Final Office Action on U.S. Appl. No. 14/392,293 dated Jun. 29, 2017.
Office Action issued on Chinese Application 201480022764.9, dated Jun. 17, 2017.
Non-Final Office Action on U.S. Appl. No. 15/626,255 dated Apr. 16, 2018.
Notice of Allowance on U.S. Appl. No. 14/392,293 dated Apr. 12, 2018.
Office Action issued on Chinese Application 201480022764.9, dated May 16, 2018.
Phoon, et al., "Tafazzin Knockdown in Mice Leads to a Developmental Cardiomyopathy With Early Diastolic Dysfunction Preceding Myocardial Noncompaction," *Journ. of American Heart Association*, vol. 1, No. 2, 14 pages (Apr. 2012).

(56) References Cited

OTHER PUBLICATIONS

Zou, et al., "An in vitro Preliminary Study of the Radio-Protective Properties of Antioxidant Peptide SS31," *Journ. of Radiation Research and Radiation Processing*, vol. 30, No. 5, pp. 291-296 (Oct. 2012), English Abstract last page.
Office Action issued in co-pending Chinese Patent Application No. 201480022767.2, dated Sep. 18, 2018.
Final Office Action issued in co-pending U.S. Appl. No. 15/626,255, dated Nov. 26, 2018.
Spinazzola, et al., "Clinical and Molecular Features of Mitochondrial DNA Depletion Syndromes," *J. Inherit Metab. Dis.*, vol. 32, pp. 143-158 (2009).
Stewart, et al., "Novel POLG1 Mutations Associated with Neuromuscular and Liver Phenotypes in Adults and Children," *J. Med. Genet.*, vol. 46, pp. 209-214 (2009).
McHugh, et al., "Sensory Ataxic Neuropathy Dysarthria and Ophthalmoparesis (Sando) in a Sibling pair with a Homozygous p. A467T Polg Mutation," *Muscle & Nerve*, pp. 265-269 (Feb. 2010).
Schulte, et al., "Ataxia with Ophthalmoplegia or Sensory Neuropathy is Frequently caused by POLG Mutations," *Neurology*, vol. 73, pp. 898-900 (Sep. 2009).
VanGoethem, "Mutation of *POLG* is Associated with Progressive External Ophthalmoplegia Characterized by mtDNA Deletions," *Nature Genetics*, vol. 28, pp. 211-212 (Jul. 2001).
Blok, et al., "The Unfolding Clinical Spectrum of POLG Mutations," *J. Med. Genet.*, vol. 46, pp. 776-785 (2009).
Ashley, et al., "Depletion of Mitochondrial DNA in Fibroblast Cultures from Patients with POLG1 Mutations is a Consequence of Catalytic Mutations," *Human Molecular Genetics*, vol. 17, No. 16, pp. 2496-2506 (2008).
Zhu, et al., "SURF1, Encoding a Factor involved in the Biogenesis of Cytochrome C Oxidase, is Mutated in Leigh Syndrome," *Nature Genetics*, vol. 20, pp. 337-343 (1998).
Tiranti, et al., "Mutations of SURF-1 in Leigh Disease Associated with Cytochrome C Oxidase Deficiency," *Am. J. Hum. Genet.*, vol. 63, pp. 1609-1621 (1998).
Dai, et al., "Mitochondrial targeted antioxidant peptide ameliorates hypertensive cardiomyopathy," Journal of the American College of Cardiology, vol. 38, No. 1, pp. 73-82 (2011).
He, et al., "Abstract 15771: Mitochondria Targeted Antioxidant Prevents Mitochondrial Dysfunction Induced by Cardiolipin Deficiency," Circulation, 2012, vol. 126, 2 pages.
Makaryan, et al. "The Cellular and Molecular Mechanisms for Neutropenia in Barth Syndrome" European Journal of Haematology, 2011, vol. 88, pp. 195-209.
Office Action in JP Patent Application No. 2019-080101 dated Apr. 13, 2020 (with English translation) (7 pages).
Office Action issued on Chinese Application 201480022767.2, dated Mar. 28, 2017, English Translation.
Phoon et al., "Tafazzin knockdown in mice leads to a developmental cardiomyopathy with early diastolic dysfunction preceding myocardial noncompaction," J. Am Heart Assoc, Apr. 2012, vol. 1, No. 2, 2 pages.
Zou et al., "An in vitro preliminary study of the radio-protective properties of antioxidant peptide SS31," Journal of Radiation Research and Radiation Proceeding, vol. 30, edition 5, pp. 291-296, Oct. 2012 (English abstract only).
Birk et al. :"Targeting cytochrome C for optimization of mitochondrial electron transport chain," The FASEB Journal, vol. 25, No. 1, Apr. 2011, 1 page.
Chinnery et la., "Mitochondrial Disorders Overview," Gene Review, Feb. 21, 2006, English translation not available.
He et al., "Abstract 15771: Mitochondria Targeted Antioxidant Prevents Mitochondrial Dysfunction Induced by Cardiolipin Deficiency," AHA Journals, 2012.
Karkucinska-Wieckowska et al., "Left Ventricular noncompaction (LVNC) and low mitochondrial membrane potential are specific for Barth syndrome," J Inherit Merab Dis, vol. 36, 2013, pp. 929-937.
Ma et al., "Superoxide Flashes, Early Mitochondrial Signals for Oxidative Stress-Induced Apoptosis," The Journal of Biological Chemistry, vol. 285, No. 31, Aug. 5, 2011, pp. 27573-25781.
Office Action issued on Japanese Application 2015-560380, dated Dec. 25, 2017, English translation not available.
Siegel et al., "Reversal of Age-Related Mitochondrial Dysfunction in vivo by Treatment with the Mitochondrially Targeted therapeutic SS-31," The FASEB Journal, vol. 26, No. 1, Apr. 2012, 1 page.
EP Search Report on EP 19190165.1 dated Feb. 5, 2020, 11 pages.
Office Action in CA Patent Application No. 2916977 dated May 27, 2020 (6 pages).
Office Action in JP Patent Application No. 2015-560380 dated Jun. 1, 2020 (with English translation) (8 pages).
Tiranti et al. "Mutations of SURF-1 in Leigh Disease Associated with Cytochrome c Oxidase Deficiency." (Dec. 1998), vol. 63, No. 6 pp. 1609-1621.
Zhu et al. "SURF1, encoding a factor involved in the biogenesis of cytochrome c oxidase, is mutated in Leigh syndrome." Nature Genetics, (Dec. 1998, vol. 20 pp. 337-343).

* cited by examiner

SEQUENCE LISTING

```
<160> NUMBER OF SEQ ID NOS: 1

<210> SEQ ID NO 1
<211> LENGTH: 10
<212> TYPE: DNA
<213> ORGANISM: Homo sapiens

<400> SEQUENCE: 1
tctgccagcc                                                          10
```

METHODS FOR THE TREATMENT OF MITOCHONDRIAL DISEASES ASSOCIATED WITH A MUTATION IN *SURF 1* OR *POLG* GENE RESULTING IN A DISRUPTION OF MITOCHONDRIAL OXIDATIVE PHOSPHORYLATION

CROSS-REFERENCE TO RELATED PATENT APPLICATIONS

This application is the U.S. 371 National Stage Application of International Application No. PCT/US2014/019645, filed Feb. 28, 2014, which claims priority to U.S. Provisional Patent Applications 61/771,534, filed Mar. 1, 2013, and 61/771,642, filed Mar. 1, 2013, which are incorporated herein by reference in their entirety.

TECHNICAL FIELD

The present technology relates generally to compositions and methods for preventing, ameliorating or treating disruption of mitochondrial function and/or the symptoms of the disruption of mitochondrial function. In particular, embodiments of the present technology relate to administering aromatic-cationic peptides in effective amounts to prevent, treat or ameliorate the disruption of mitochondrial oxidative phosphorylation or symptoms thereof, in a cell such as that found in a subject suffering from, or predisposed to, a mitochondrial disease or disorder associated with mutations in the surfeit locus protein 1 (SURF1) gene or DNA polymerase gamma (POLG) gene.

BACKGROUND

The following description is provided to assist the understanding of the reader. None of the information provided or references cited is admitted to be prior art.

Mitochondria (plural for mitochondrion) are sometimes described as cellular "power plants" because among other things, mitochondria are responsible for creating more than 90% of the energy needed by the body to sustain life and support growth. Mitochondria are organelles found in almost every cell in the body and are responsible for creating more than 90% of cellular energy. They are necessary to the body to sustain life and support growth. In addition to making energy, mitochondria are also deeply involved in a variety of other activities, such as making steroid hormones and manufacturing the building blocks of DNA. Mitochondrial failure causes cell injury that leads to cell death.

Mitochondrial diseases are nearly as common as childhood cancer. Approximately one in 4,000 children born in the United States every year will develop a mitochondrial disorder by age 10. In adults, many diseases of aging have been found to have defects of mitochondrial function. These include, but are not limited to, type 2 diabetes, Parkinson's disease, atherosclerotic heart disease, stroke, Alzheimer's disease, and cancer. In addition, select drugs can injure the mitochondria.

There are multiple forms of mitochondrial disease. Mitochondrial disease can manifest as a chronic, genetic disorder that occurs when the mitochondria of the cell fails to produce enough energy for cell or organ function. Indeed, for many patients, mitochondrial disease is an inherited condition that runs in families (genetic). Mitochondrial disease is inherited in a number of different ways, for example, autosomal inheritance, mitochondrial DNA (mtDNA) inheritance, and combinations thereof. For example, mutations of SURF1 and/or POLG genes can contribute to mitochondrial disease in humans. In addition, some patients acquire mitochondrial dysfunction or disease due to other factors, including mitochondrial toxins.

Mitochondrial disease presents very differently from individual to individual. There is presently no cure for mitochondrial-based disease. Treatment is generally palliative to improve disease symptoms. Treatment often includes of vitamin therapy and conserving energy. Treatment may involve special diets and/or a combination of vitamins, and reducing any stress on the body.

SUMMARY

The present technology relates to the prevention, treatment or amelioration of mitochondrial disease and its symptoms, e.g., such as conditions associated with mutations in the SURF1 gene or POLG gene in mammals or mammalian cells, through administration of therapeutically effective amounts of aromatic-cationic peptides, such as D-Arg-2',6'-Dmt-Lys-Phe-NH$_2$, or pharmaceutically acceptable salts thereof, such as acetate salt or trifluoroacetate salt, to subjects in need thereof. In some aspects, the present technology relates to preventing, treating or ameliorating the disruption of mitochondrial oxidative phosphorylation associated with mutations in the SURF1 gene or POLG gene in a subject in need thereof, or in mammalian cells in need thereof, by administering aromatic-cationic peptides as disclosed herein. In some embodiments, the mammalian subject is at risk for, or suffering from or at increased risk of a disease or condition characterized by mitochondrial dysfunction associated with mitochondrial gene mutations. In some embodiments, the subject is suffering from or at increased risk of a disease or conditions characterized by a gene mutation which affects mitochondrial function. In some embodiments, the disruption of mitochondrial oxidative phosphorylation is associated with at least one gene mutation. In some embodiments, the subject is suffering from or at increased of a disease or conditions characterized by a mutation in SURF1. In some embodiments, the subject is suffering from or at increased of a disease or conditions characterized by a mutation in POLG.

In some embodiments, the mammalian cell is either in situ or ex vivo. In some embodiments, the disruption of mitochondrial oxidative phosphorylation is due to impairment of the complete assembly of at least one mitochondrial polypeptide, such as Complex I; Complex II; Complex III; Complex IV; and Complex V and combinations thereof. In some embodiments, the disruption of mitochondrial oxidative phosphorylation is due to impairment of a mitochondrial supercomplex assembly.

Also disclosed herein are methods for treating or ameliorating a mitochondrial disease or disorder in a subject in need thereof, the method comprising: administering a therapeutically effective amount of a peptide D-Arg-2',6'-Dmt-Lys-Phe-NH$_2$ or a pharmaceutically acceptable salt thereof, thereby treating or ameliorating at least one symptom of the mitochondrial disease or condition.

In some embodiments, symptoms of mitochondrial disease are prevented, treated or ameliorated. In some embodiments of the disclosed methods, the symptoms of a mitochondrial disease, condition or disorder may include any one or more of the following: poor growth, loss of muscle coordination, muscle weakness, neurological deficit, seizures, autism, autistic spectrum, autistic-like features, learning disabilities, heart disease, liver disease, kidney disease, gastrointestinal disorders, severe constipation, diabetes, increased risk of infection, thyroid dysfunction, adrenal dysfunction, autonomic dysfunction, confusion, disorientation, memory loss, poor growth, failure to thrive, poor coordination, sensory (vision, hearing) problems, reduced mental functions, disease of the organ, dementia, respiratory problems, hypoglycemia, apnea, lactic acidosis, seizures, swallowing difficulties, developmental delays, movement disorders (dystonia, muscle spasms, tremors, chorea), stroke, and brain atrophy.

In some embodiments of the disclosed methods, the mitochondrial disease or condition may include one or more of the following: Leigh syndrome, Alpers' disease, ataxia-neuropathy disorders, and progressive external ophthalmoplegia.

In some embodiments of the disclosed methods, the mitochondrial disease or condition is associated with at least one gene mutation. In some embodiments of the disclosed methods, the gene mutation is located in one or more of the SURF1 or POLG gene.

In some aspects, methods for increasing an uncoupling ratio of a mammalian cell are provided. In some embodiments, the methods include: contacting the cell with a therapeutically effective amount of a peptide D-Arg-2',6'-Dmt-Lys-Phe-NH$_2$ or a pharmaceutically acceptable salt thereof, thereby increasing the uncoupling ratio of the cell. In some embodiments, the cell is a human cell. In some embodiments, the cell is in a human subject.

In some aspects, the disclosure provides methods for the prevention, treatment or amelioration of mitochondrial disease or conditions or symptoms thereof, comprising administering to a subject in need thereof a therapeutically effective amount of an aromatic-cationic peptide or a pharmaceutically acceptable salt thereof, e.g., D-Arg-2',6'-Dmt-Lys-Phe-NH$_2$, or pharmaceutically acceptable salts thereof, such as acetate salt or trifluoroacetate salt. In some embodiments, the method further comprises administration of one or more additional therapeutic agents. In some embodiments, the aromatic-cationic peptide is a peptide having:

at least one net positive charge;
a minimum of four amino acids;
a maximum of about twenty amino acids;
a relationship between the minimum number of net positive charges ($p_m$) and the total number of amino acid residues (r) wherein $3p_m$ is the largest number that is less than or equal to r+1; and a relationship between the minimum number of aromatic groups (a) and the total number of net positive charges ($p_t$) wherein 2a is the largest number that is less than or equal to $p_t$+1, except that when a is 1, $p_t$ may also be 1. In particular embodiments, the subject is a human.

In some embodiments, $2p_m$ is the largest number that is less than or equal to r+1, and a may be equal to $p_t$. The aromatic-cationic peptide may be a water-soluble peptide having a minimum of two or a minimum of three positive charges. In some embodiments, the peptide comprises one or more non-naturally occurring amino acids, for example, one or more D-amino acids. In some embodiments, the C-terminal carboxyl group of the amino acid at the C-terminus is amidated. In certain embodiments, the peptide has a minimum of four amino acids. The peptide may have a maximum of about 6, a maximum of about 9, or a maximum of about 12 amino acids.

In some embodiments, the peptide comprises a tyrosine or a 2',6'-dimethyltyrosine (Dmt) residue at the N-terminus. For example, the peptide may have the formula Tyr-D-Arg-Phe-Lys-NH$_2$ or 2',6'-Dmt-D-Arg-Phe-Lys-NH$_2$. In another embodiment, the peptide comprises a phenylalanine or a 2',6'-dimethylphenylalanine residue at the N-terminus. For example, the peptide may have the formula Phe-D-Arg-Phe-Lys-NH$_2$ or 2',6'-Dmp-D-Arg-Phe-Lys-NH$_2$. In a particular embodiment, the aromatic-cationic peptide has the formula D-Arg-2',6'-Dmt-Lys-Phe-NH$_2$ or a pharmaceutically acceptable salt thereof such as acetate salt or trifluoroacetate salt.

In one embodiment, the peptide is defined by formula I:

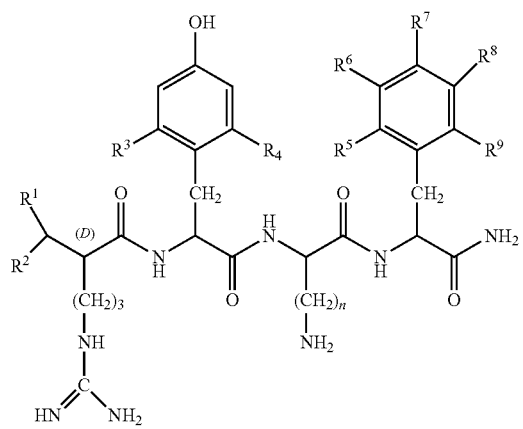

wherein $R^1$ and $R^2$ are each independently selected from
(i) hydrogen;
(ii) linear or branched $C_1$-$C_6$ alkyl;

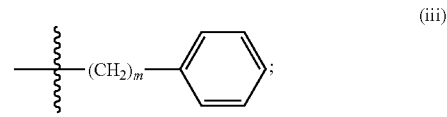

where $m$ = 1-3

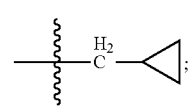

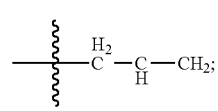

$R^3$ and $R^4$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo;

$R^5$, $R^6$, $R^7$, $R^8$, and $R^9$ are each independently selected from
(i) hydrogen;
(ii) linear or branched $C_1$-$C_6$ alkyl;
(iii) $C_1$-$C_6$ alkoxy;
(iv) amino;

(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo; and n is an integer from 1 to 5.

In a particular embodiment, $R^1$ and $R^2$ are hydrogen; $R^3$ and $R^4$ are methyl; $R^5$, $R^6$, $R^7$, $R^8$, and $R^9$ are all hydrogen; and n is 4.

In one embodiment, the peptide is defined by formula II:

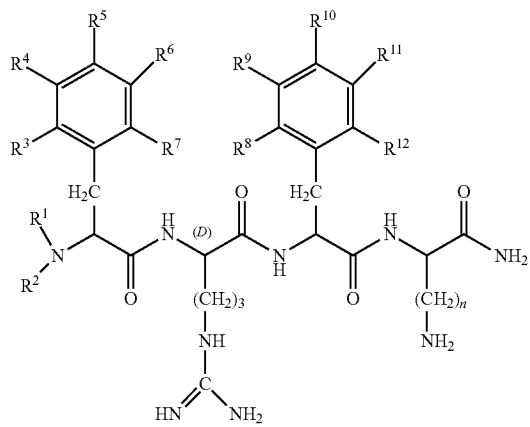

wherein $R^1$ and $R^2$ are each independently selected from
(i) hydrogen;
(ii) linear or branched $C_1$-$C_6$ alkyl;

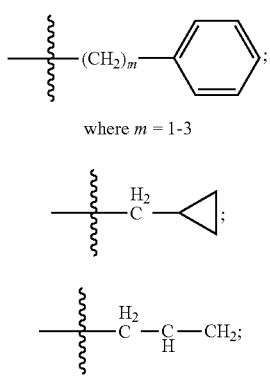

$R^3$, $R^4$, $R^5$, $R^6$, $R^7$, $R^8$, $R^9$, $R^{10}$, $R^{11}$ and $R^{12}$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo; and n is an integer from 1 to 5.

In a particular embodiment, $R^1$, $R^2$, $R^3$, $R^4$, $R^5$, $R^6$, $R^7$, $R^8$, $R^9$, $R^{10}$, $R^{11}$ and $R^{12}$ are all hydrogen; and n is 4. In another embodiment, $R^1$, $R^2$, $R^3$, $R^4$, $R^5$, $R^6$, $R^7$, $R^8$, $R^9$, and $R^{11}$ are all hydrogen; $R^8$ and $R^{12}$ are methyl; $R^{10}$ is hydroxyl; and n is 4.

The aromatic-cationic peptides may be administered in a variety of ways. In some embodiments, the peptides may be administered orally, topically, intranasally, intraperitoneally, intravenously, subcutaneously, or transdermally (e.g., by iontophoresis). In some embodiments, the aromatic-cationic peptide is administered by an intracoronary route or an intra-arterial route.

In one embodiment, the present technology provides methods for the prevention, treatment or amelioration of mitochondrial disease or conditions or symptoms thereof in a mammalian subject in need thereof, and/or treating, preventing or ameliorating the disruption of mitochondrial oxidative phosphorylation in a subject in need thereof, by administering aromatic-cationic peptides as disclosed herein, the method comprising administering to the subject a therapeutically effective amount of a peptide D-Arg-2',6'-Dmt-Lys-Phe-$NH_2$ or a pharmaceutically acceptable salt thereof, such as acetate salt or trifluoroacetate salt, thereby ameliorating or treating mitochondrial disease, defects, or conditions, and/or signs or symptoms thereof. In one embodiment, the method further comprises the step administering one or more additional therapeutic agents to the subject. In one embodiment, the mammalian subject is at risk for, or suffering from or at increased risk of a disease or condition characterized by mitochondrial dysfunction. In some embodiments, the subject is suffering from or at increased risk of a disruption of mitochondrial oxidative phosphorylation. In some embodiments, the subject is suffering from or at increased of a disease or conditions characterized by a genetic mutation which affects mitochondrial function. In some embodiments, the subject is suffering from or at increased of a disease or conditions characterized by a mutation in SURF1. In some embodiments, the subject is suffering from or at increased of a disease or conditions characterized by a mutation in POLG. In some embodiments, the subject is treated by administering an aromatic-cationic peptide as disclosed herein.

In another aspect, the present technology relates to methods for treating Leigh syndrome in a subject in need thereof, the method comprising: administering a therapeutically effective amount of the peptide D-Arg-2',6'-Dmt-Lys-Phe-NH2 or a pharmaceutically acceptable salt thereof.

In another aspect, the present technology relates to methods for treating Alpers' disease in a subject in need thereof, the method comprising: administering a therapeutically effective amount of the peptide D-Arg-2',6'-Dmt-Lys-Phe-NH2 or a pharmaceutically acceptable salt thereof.

In another aspect, the present technology relates to methods for treating ataxia-neuropathy disorders in a subject in need thereof, the method comprising: administering a therapeutically effective amount of the peptide D-Arg-2',6'-Dmt-Lys-Phe-NH2 or a pharmaceutically acceptable salt thereof.

In another aspect, the present technology relates to methods for treating progressive external ophthalmoplegia in a subject in need thereof, the method comprising: administering a therapeutically effective amount of the peptide D-Arg-2',6'-Dmt-Lys-Phe-NH2 or a pharmaceutically acceptable salt thereof.

In some embodiments, anyone of the above methods of treatment reduces or ameliorates one or more symptoms selected from the group consisting of poor growth, loss of muscle coordination, muscle weakness, neurological deficit, seizures, autism, autistic spectrum, autistic-like features, learning disabilities, heart disease, liver disease, kidney disease, gastrointestinal disorders, severe constipation, diabetes, increased risk of infection, thyroid dysfunction, adrenal dysfunction, autonomic dysfunction, confusion, disorientation, memory loss, poor growth, failure to thrive, poor coordination, sensory (vision, hearing) problems, reduced mental functions, disease of the organ, dementia, respiratory problems, hypoglycemia, apnea, lactic acidosis, seizures, swallowing difficulties, developmental delays, movement disorders (dystonia, muscle spasms, tremors, chorea), stroke, and brain atrophy.

In some embodiments, the peptide of anyone of the above methods of treatment is administered orally, topically, systematically, intravenously, subcutaneously, intraperitoneally, or intramuscularly.

In some embodiments, the Leigh syndrome is associated with a SURF1 gene mutation. In some embodiments, the SURF 1 mutation results in a disruption of mitochondrial oxidative phosphorylation due to impairment of the complete assembly of at least one mitochondrial complex selected from the group consisting of: Complex I; Complex II; Complex III; Complex IV; and Complex V.

In some embodiments, the subject with Alper's disease, ataxia-neuropathy disorders, or progressive external ophthalmoplegia has a POLG mutation that results in a disruption of mitochondrial oxidative phosphorylation.

DETAILED DESCRIPTION

Figure 1:
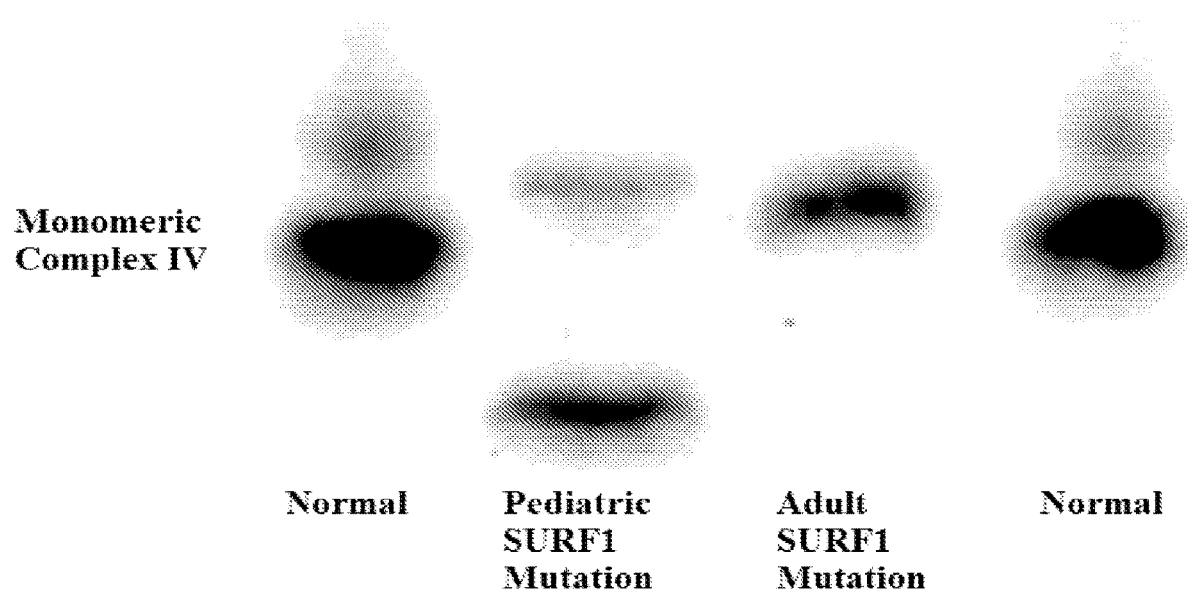
FIG. 1 is an electrophoretic gel illustrating Complex IV monomeric OXPHOS enzyme assembly in subjects with SURF1 mutation.
Figure 2A:
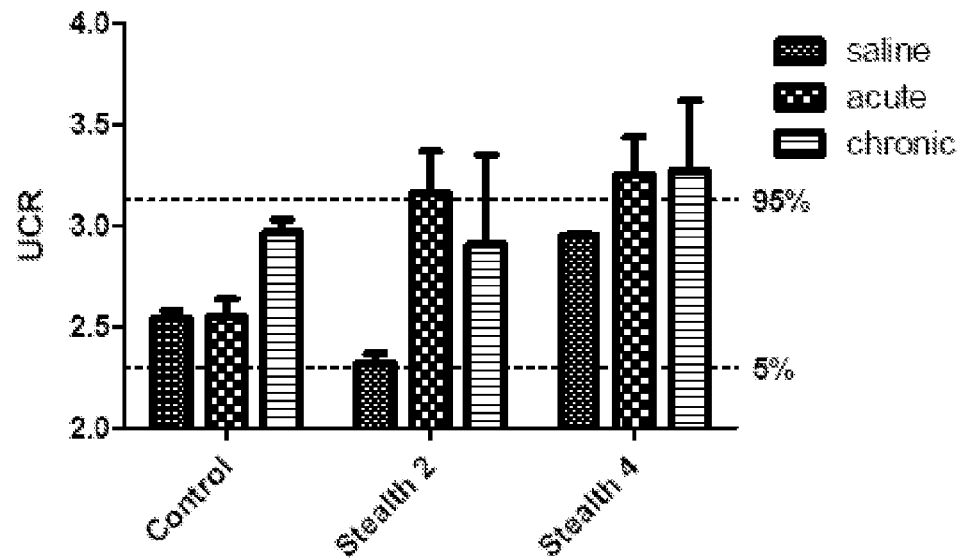
FIGS. 2A-G are charts illustrative of the effect of SS-31 on OXPHOS capacity in transformed fibroblasts that express mutated SURF1 or POLG. "Stealth 2" in the figures is the name of the fibroblast cell line carrying the SURF1 mutant; "Stealth 4" in the figures is the name of the fibroblast cell line carrying the POLG mutant.
Figure 2A:
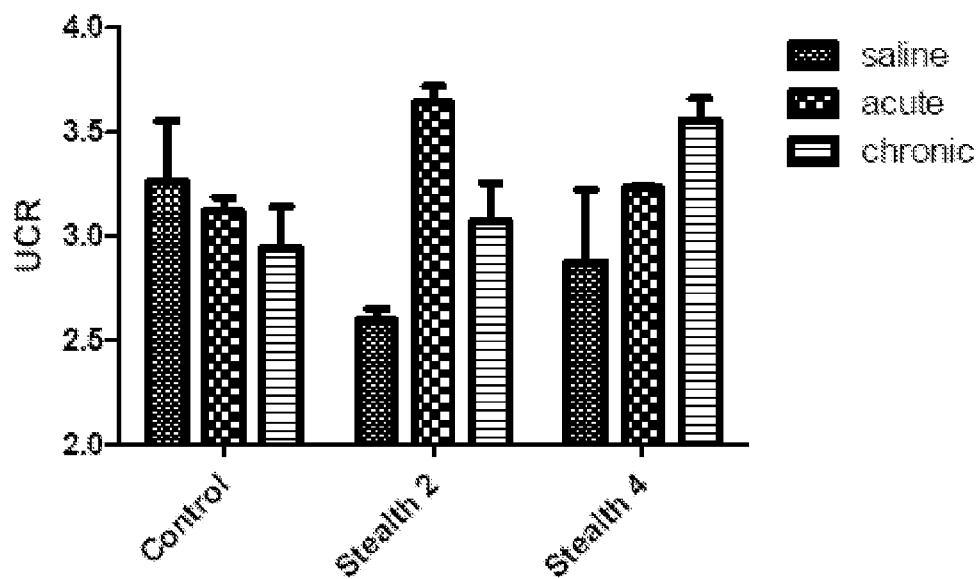
Figure 2B:
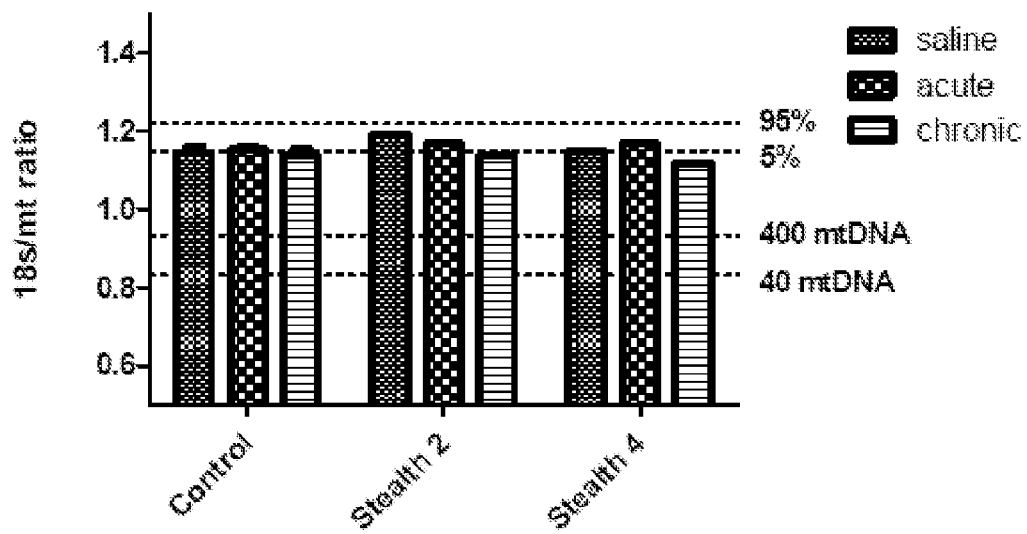
Figure 2B:
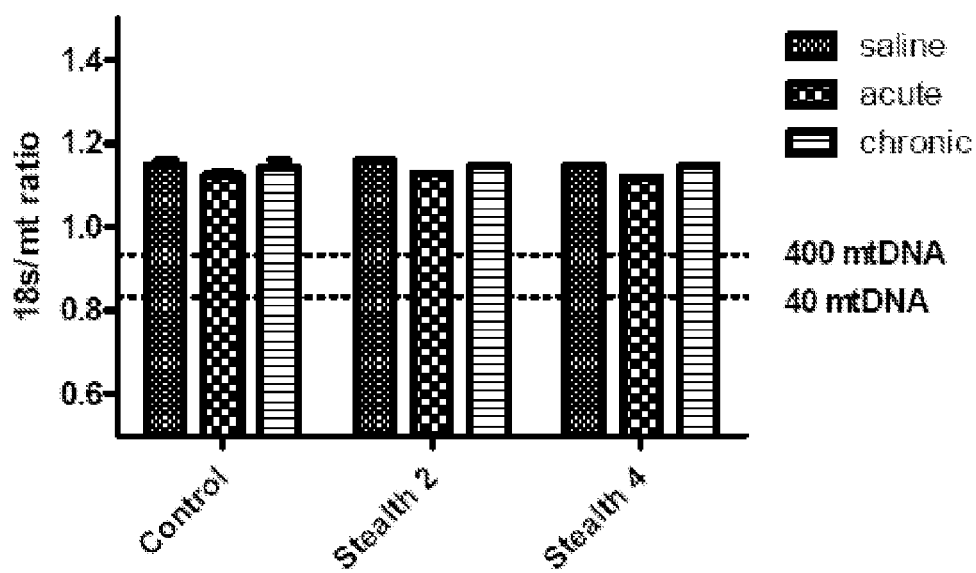
Figure 2C:
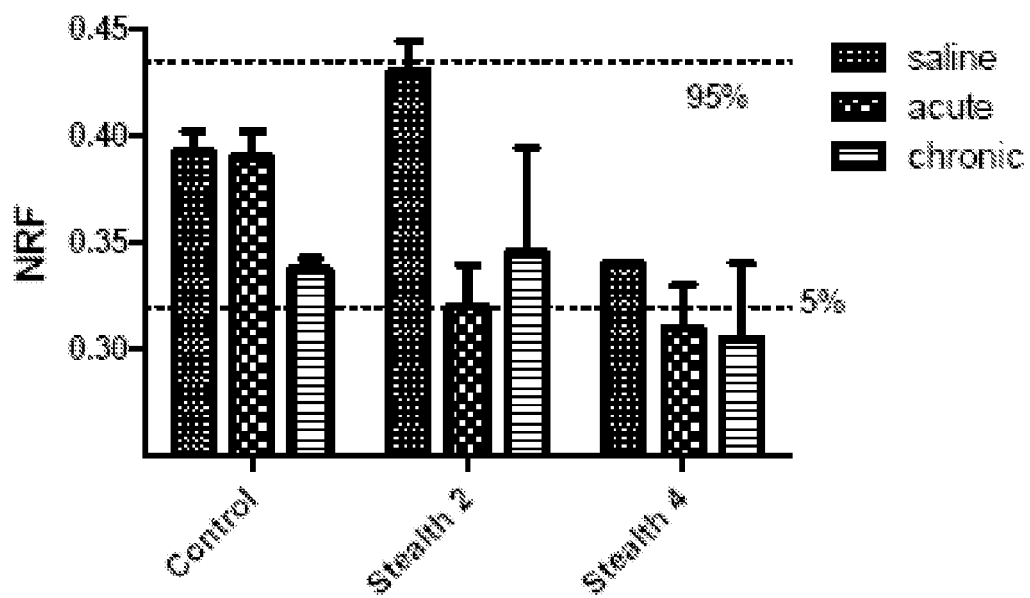
Figure 2C:
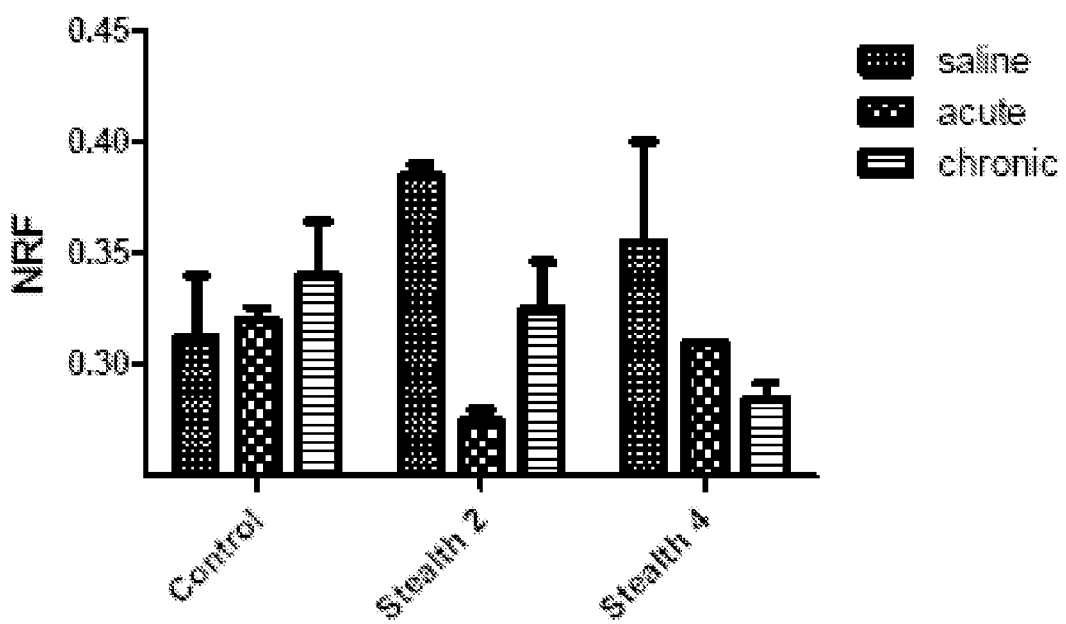
Figure 2D:
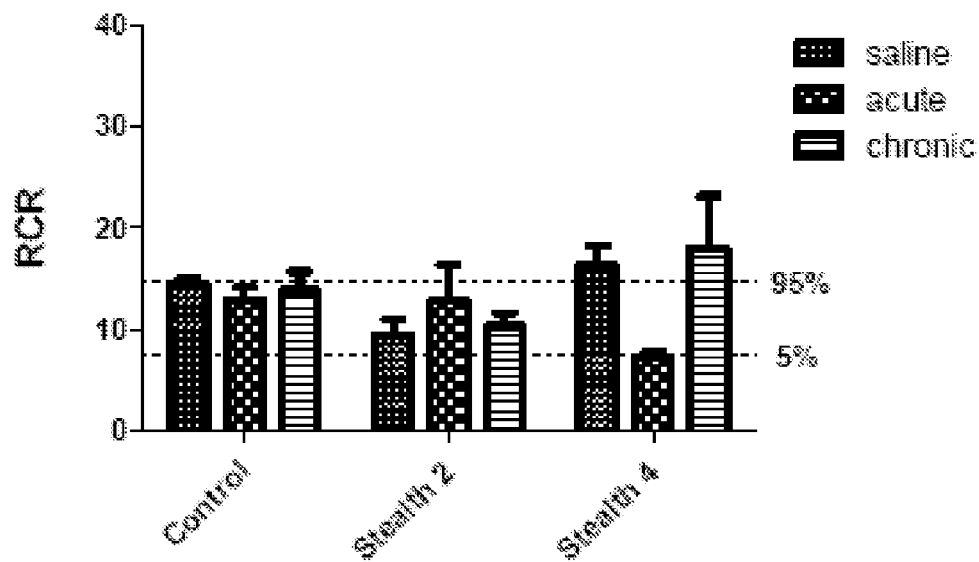
Figure 2D:
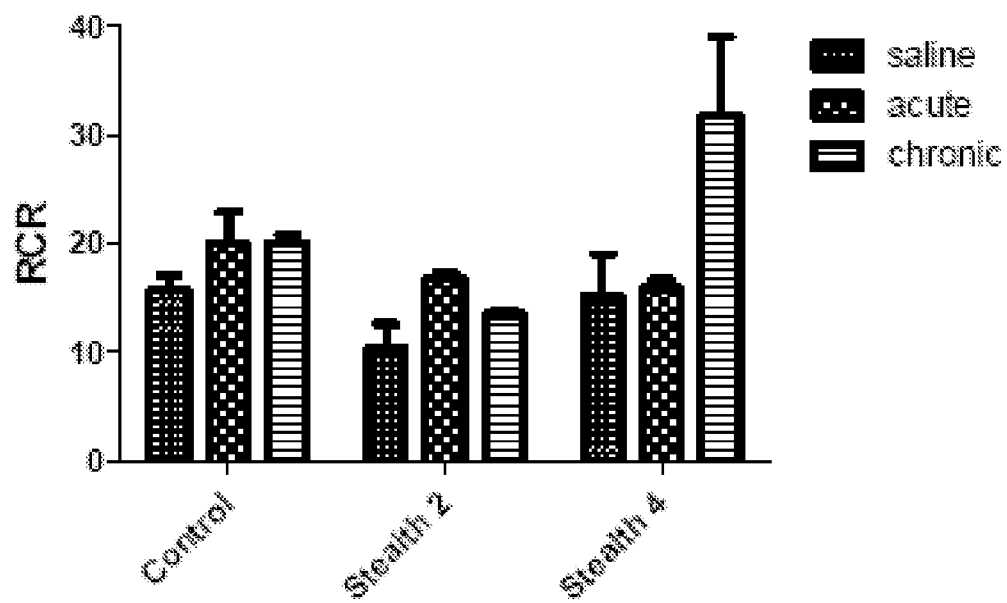
Figure 2E:
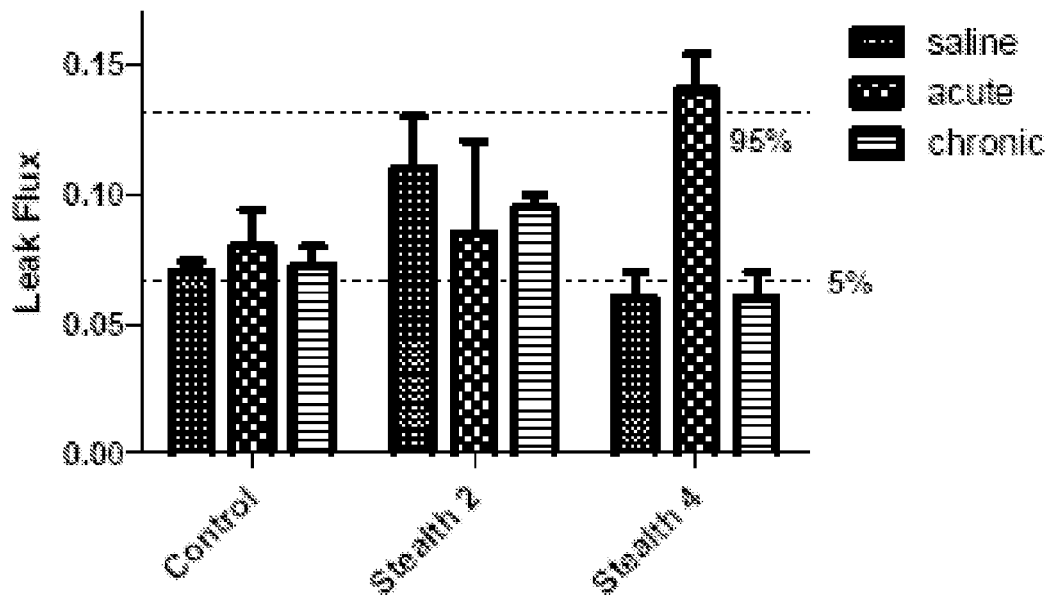
Figure 2E:
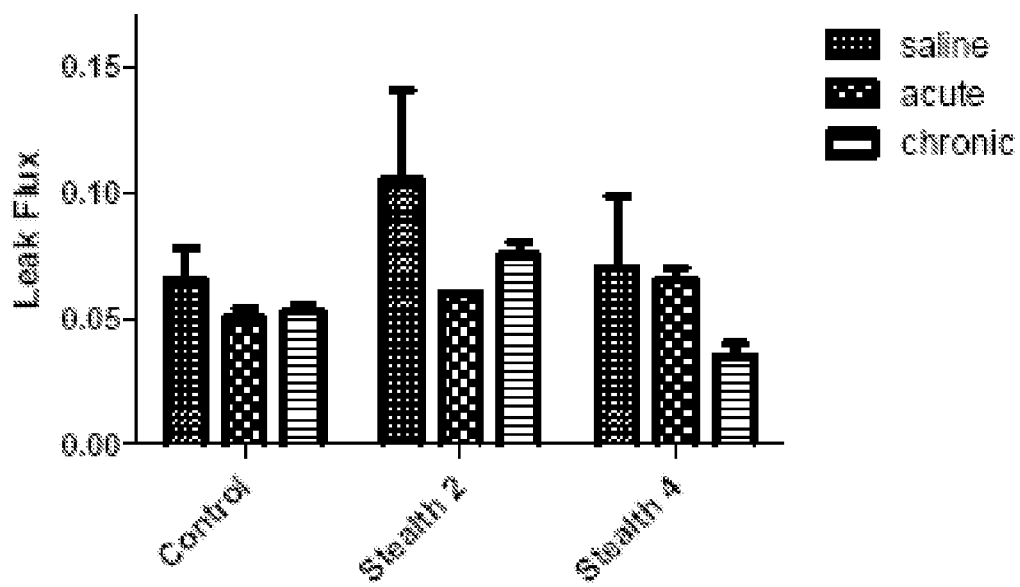
Figure 2F:
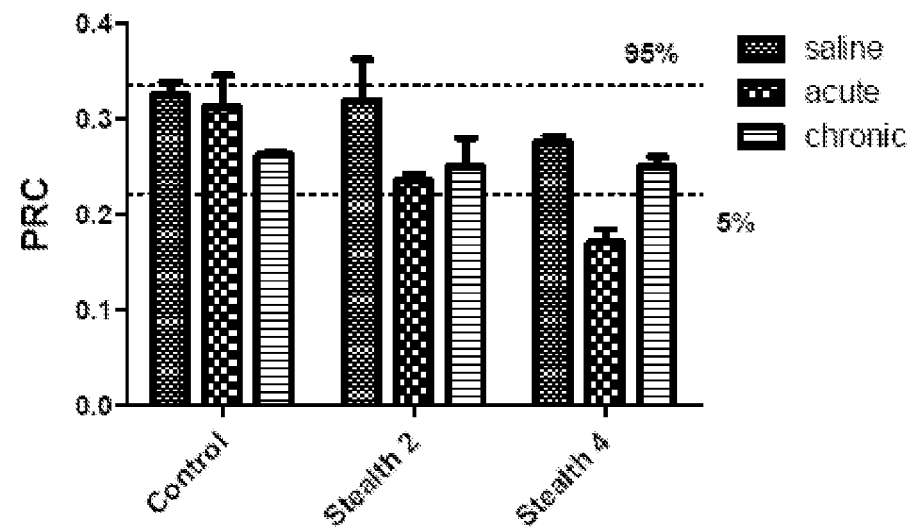
Figure 2F:
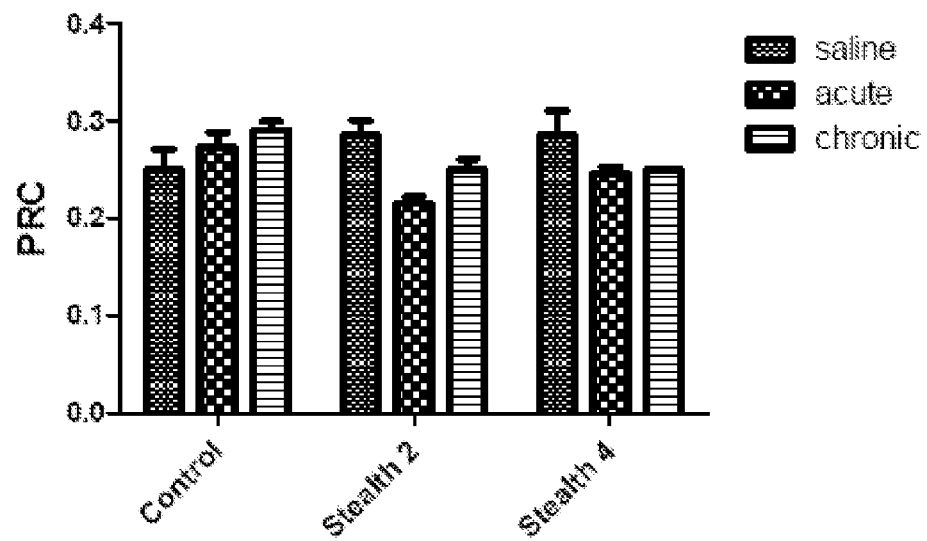
Figure 2G:
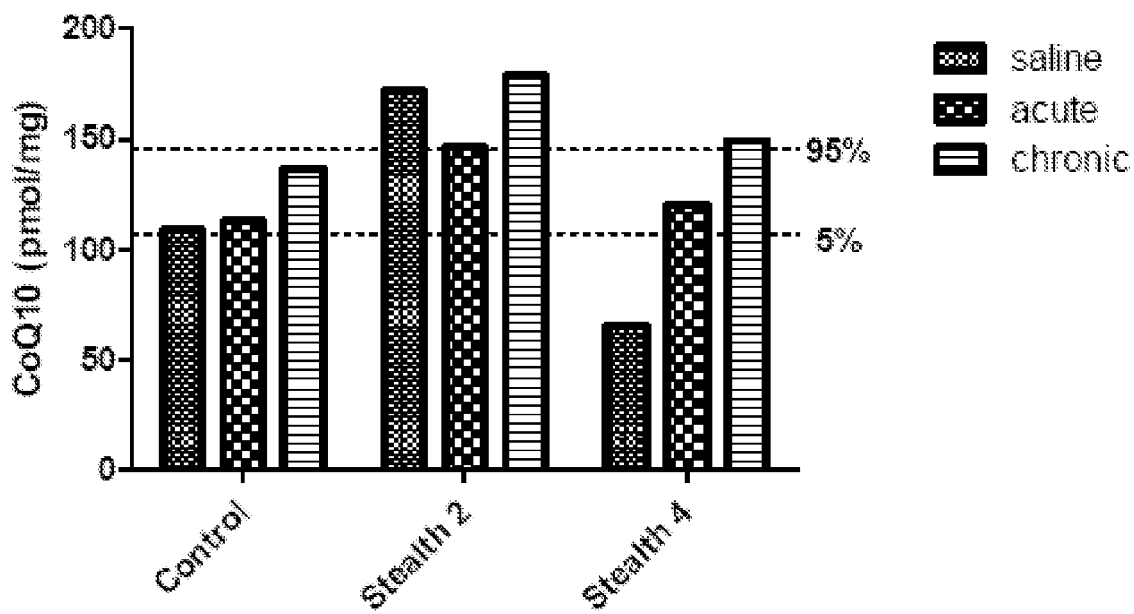
Figure 2G:
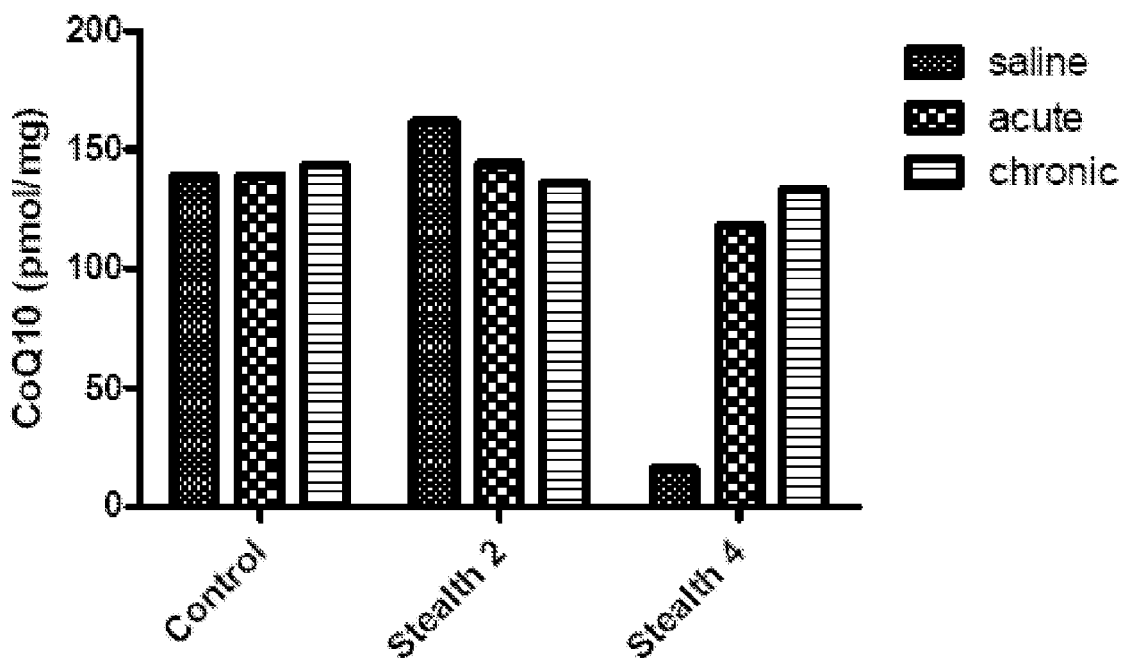
Figure 3A:
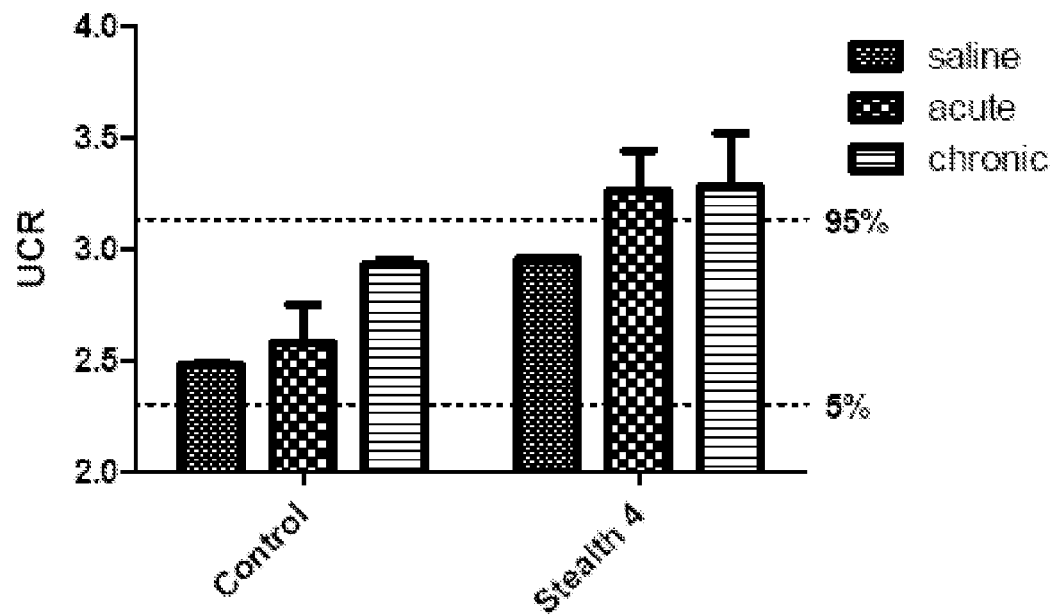
FIGS. 3A-G are charts illustrative of the effect of SS-31 on OXPHOS capacity in transformed fibroblasts that express mutated POLG (cell line "Stealth 4").
Figure 3A:
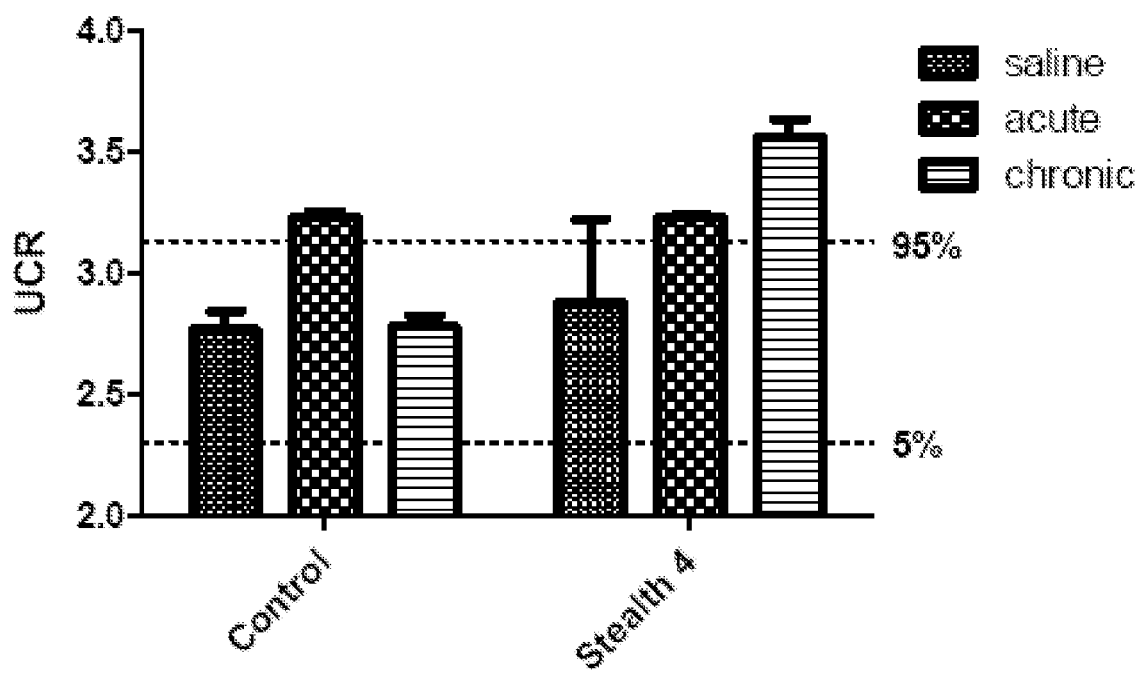
Figure 3B:
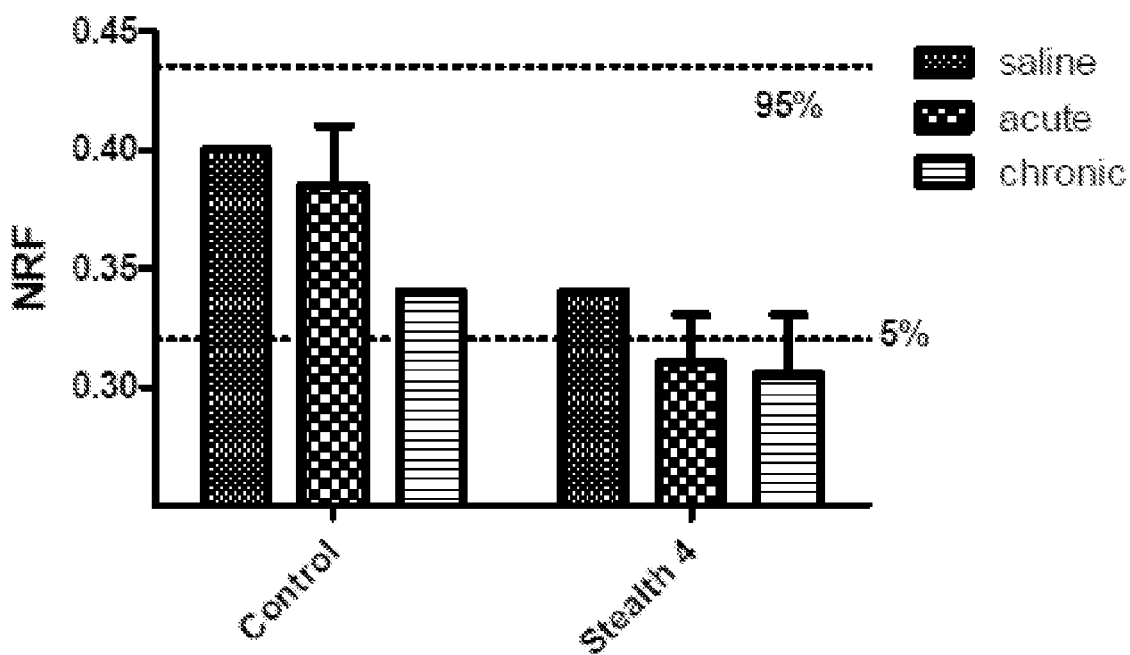
Figure 3B:
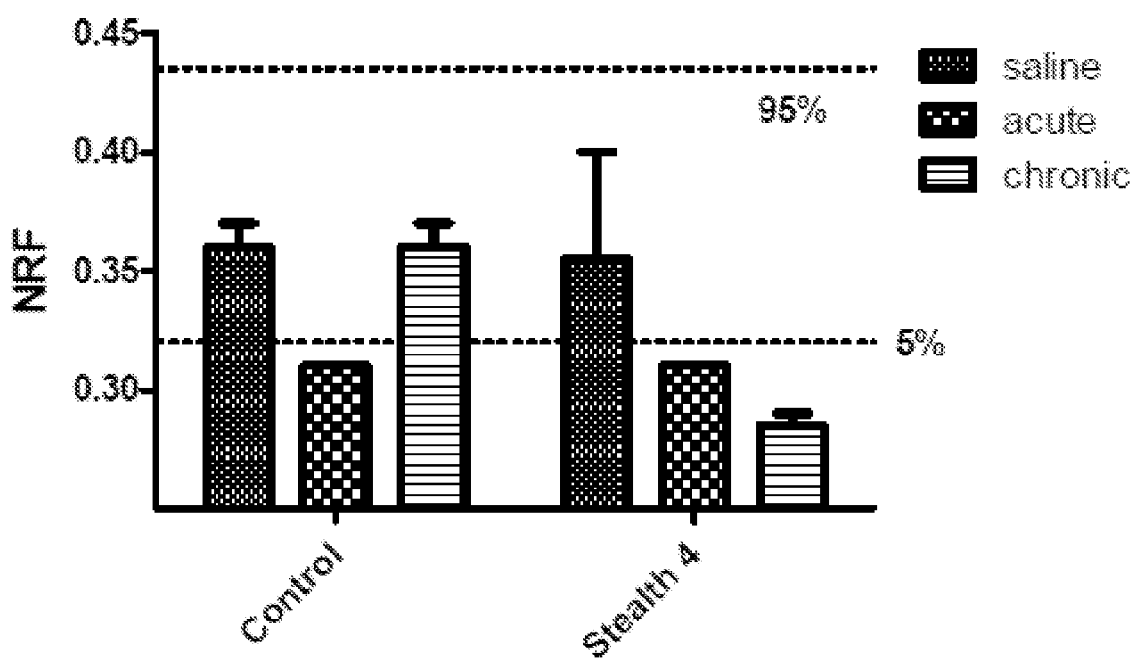
Figure 3C:
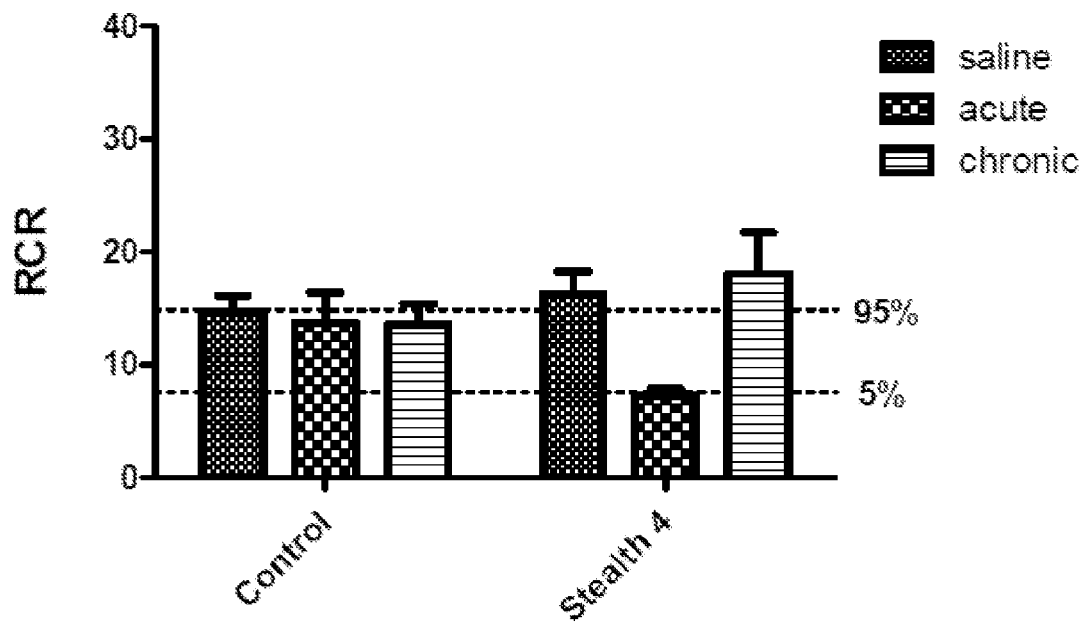
Figure 3C:
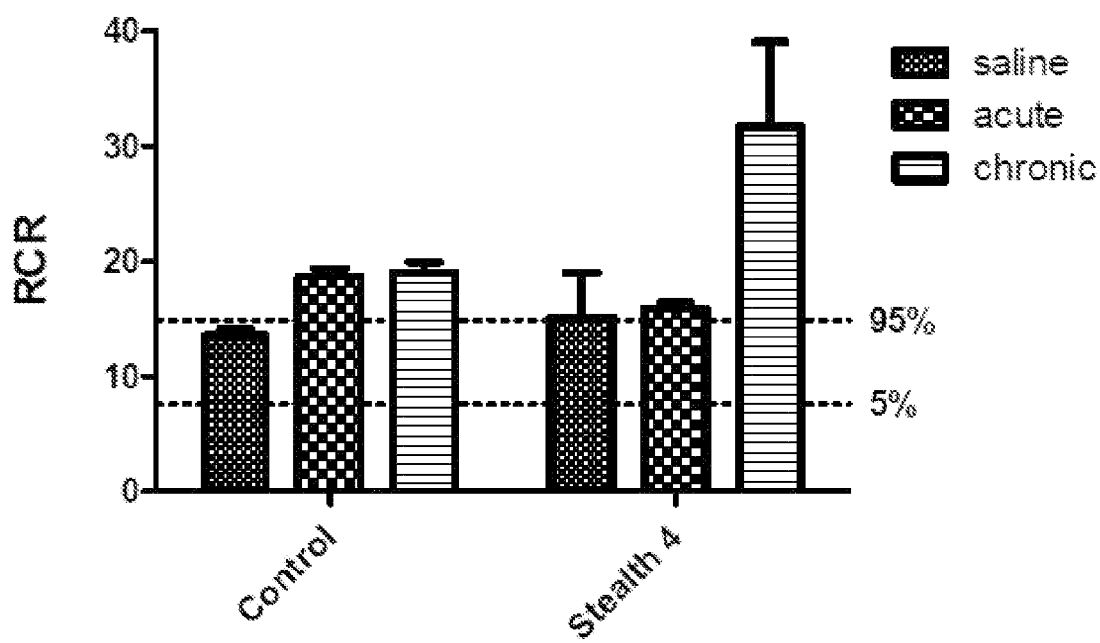
Figure 3D:
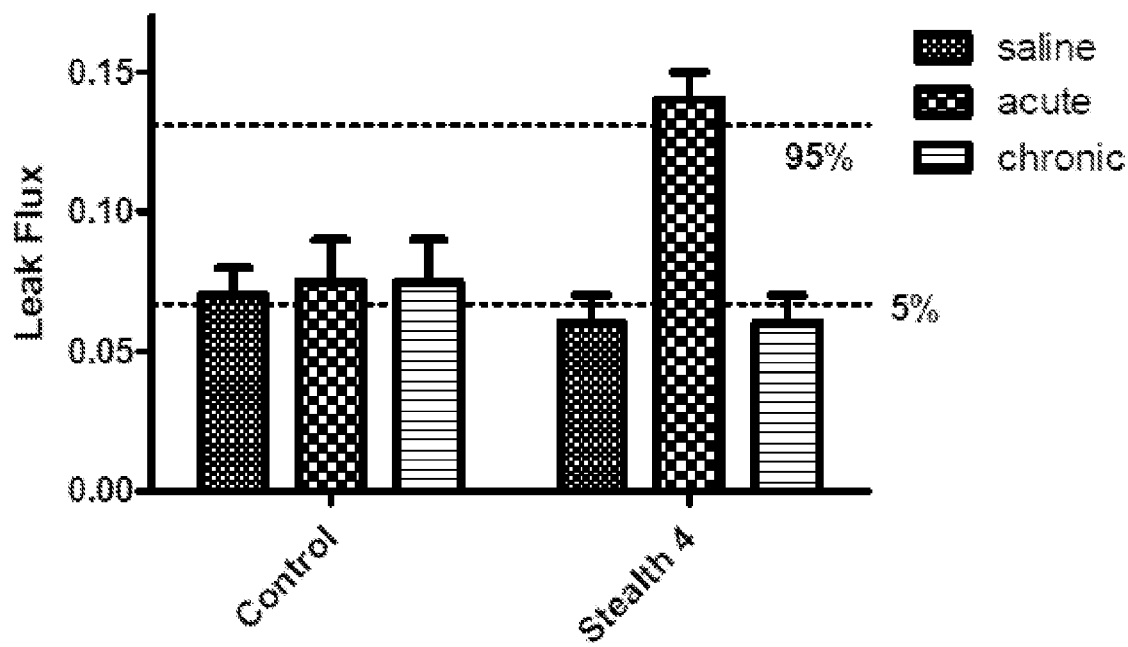
Figure 3D:
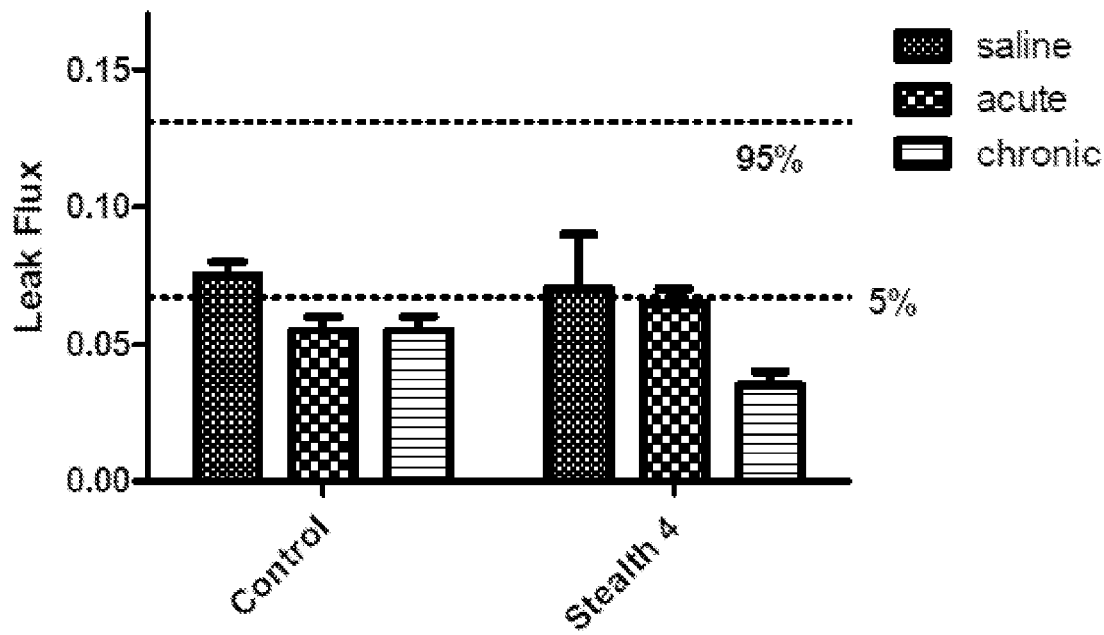
Figure 3E:
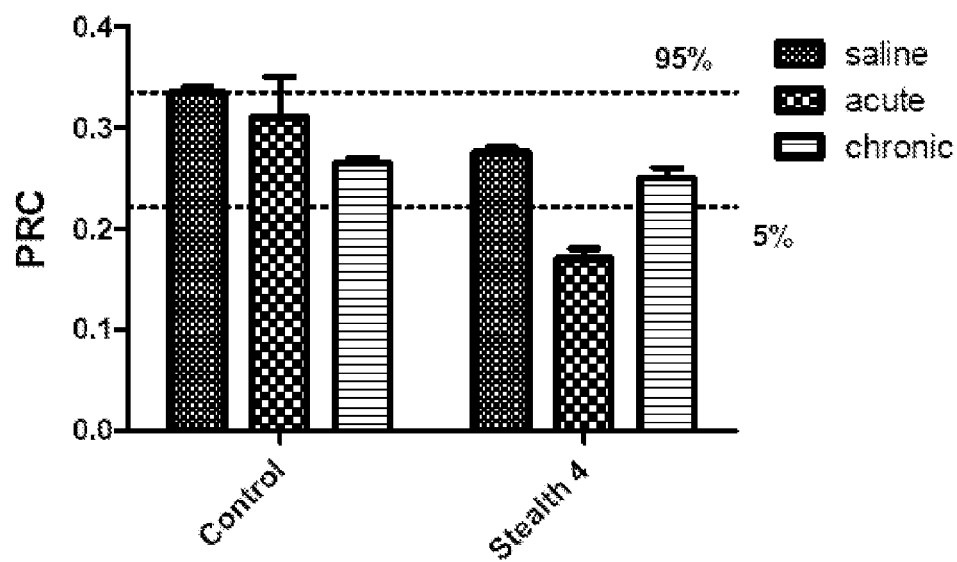
Figure 3E:
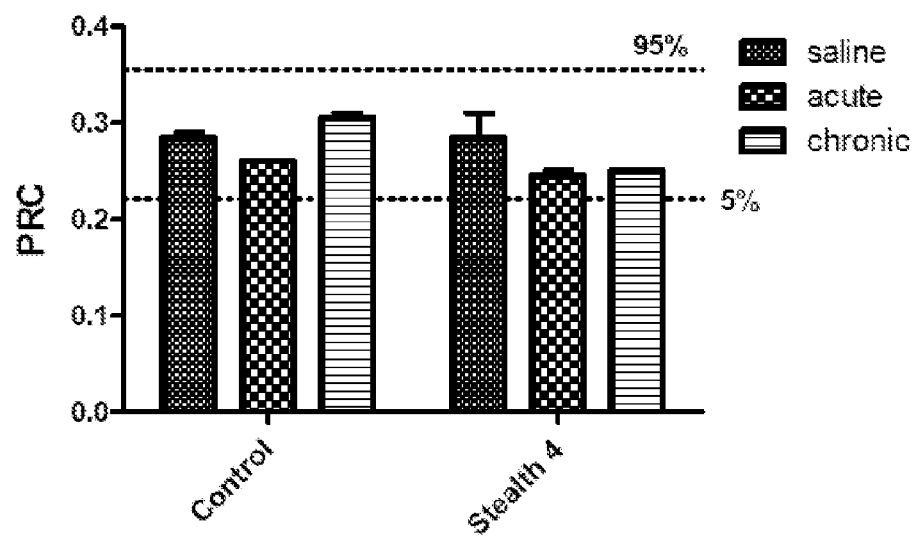
Figure 3F:
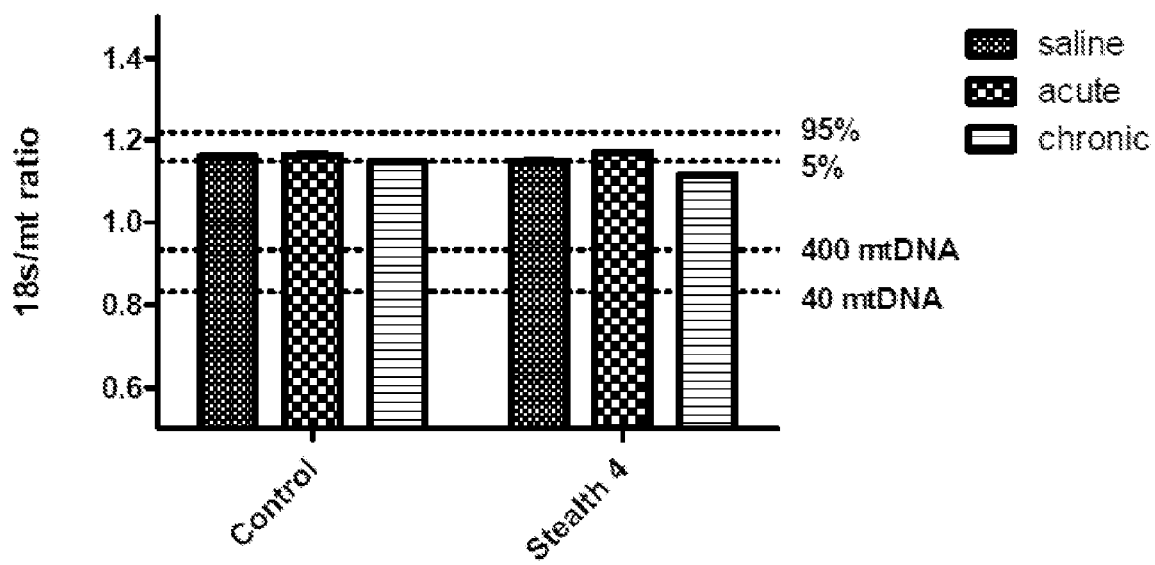
Figure 3F:
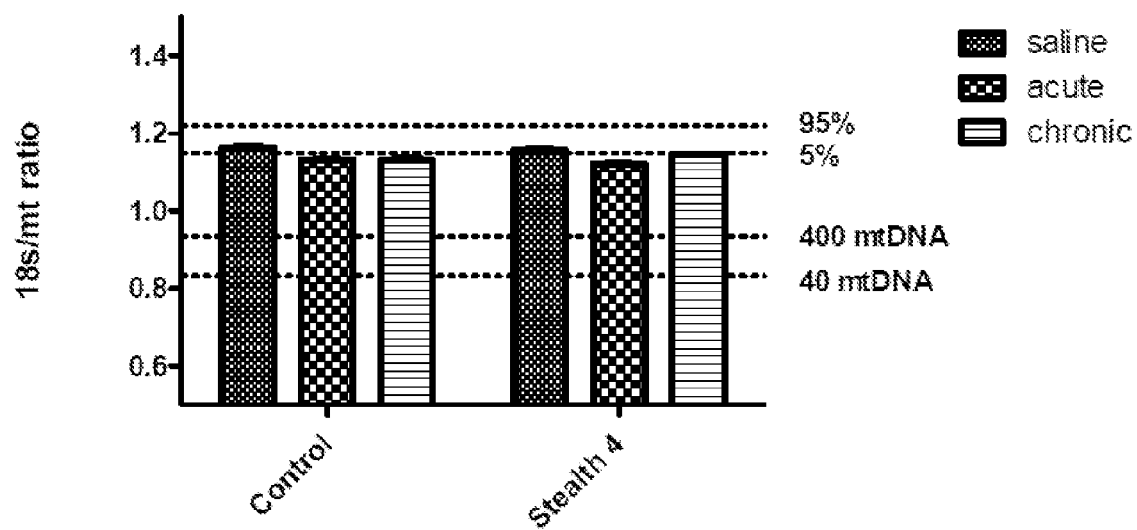
Figure 3G:
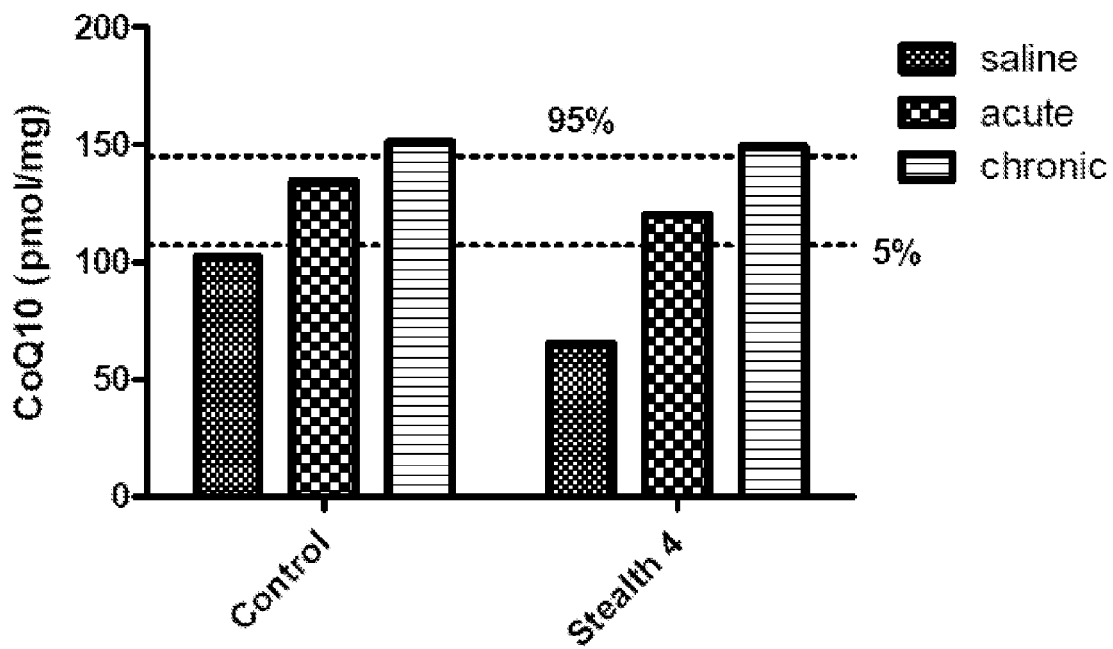
Figure 3G:
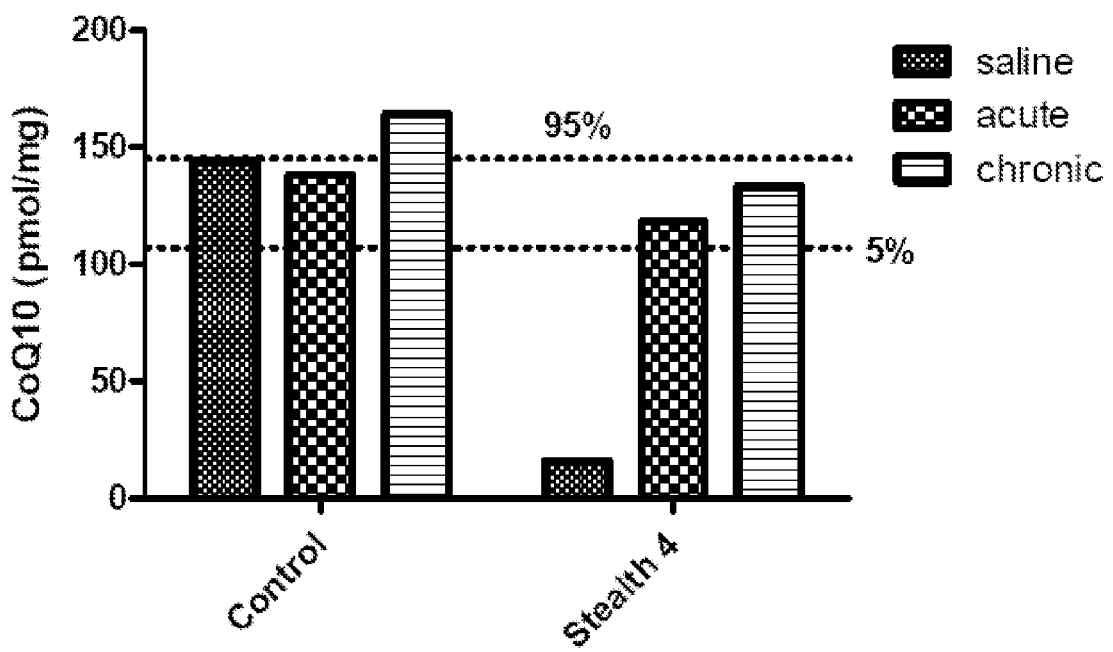
Figure 4:
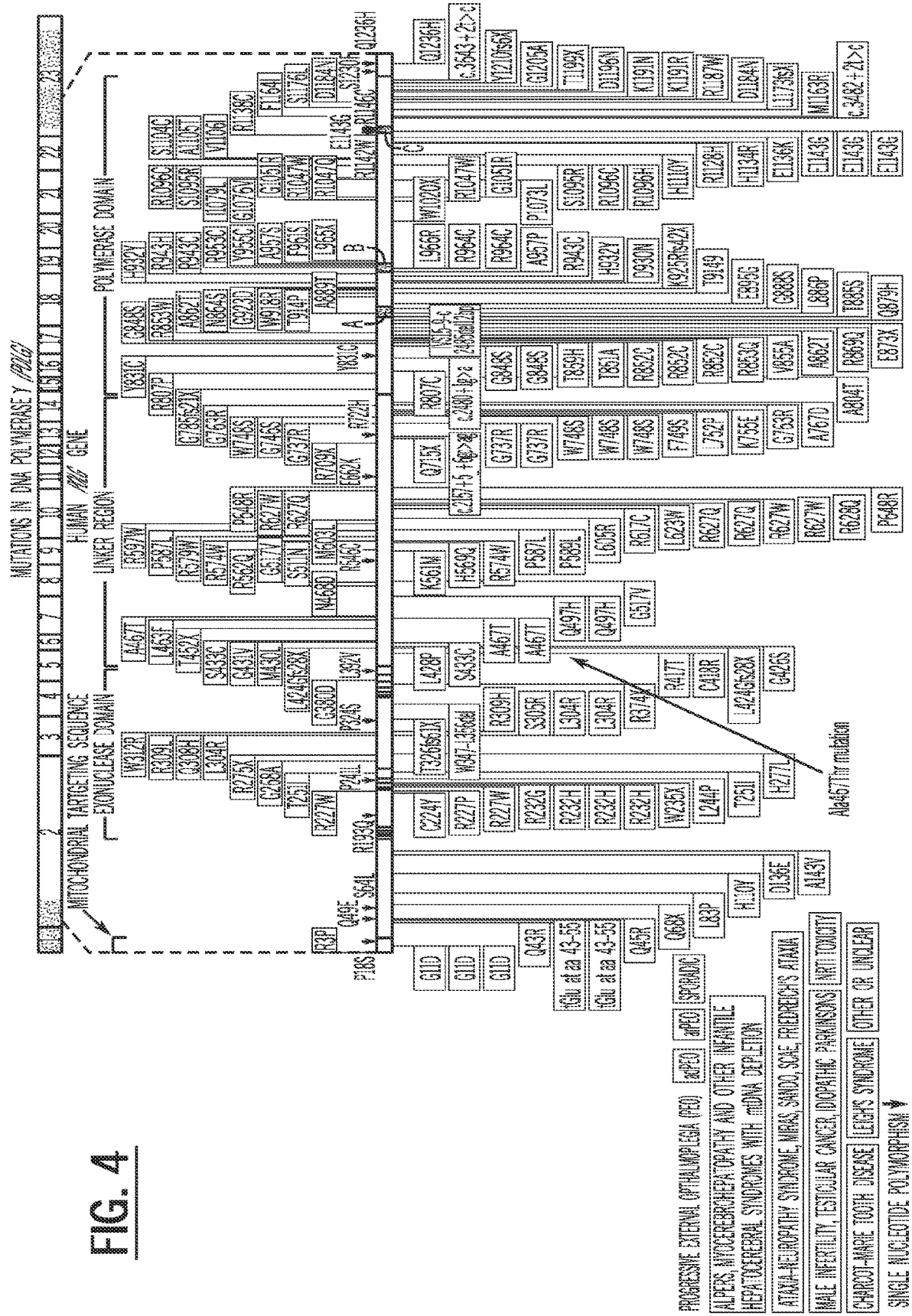
FIG. 4 provides a list of exemplary POLG mutations.
Figure 5:
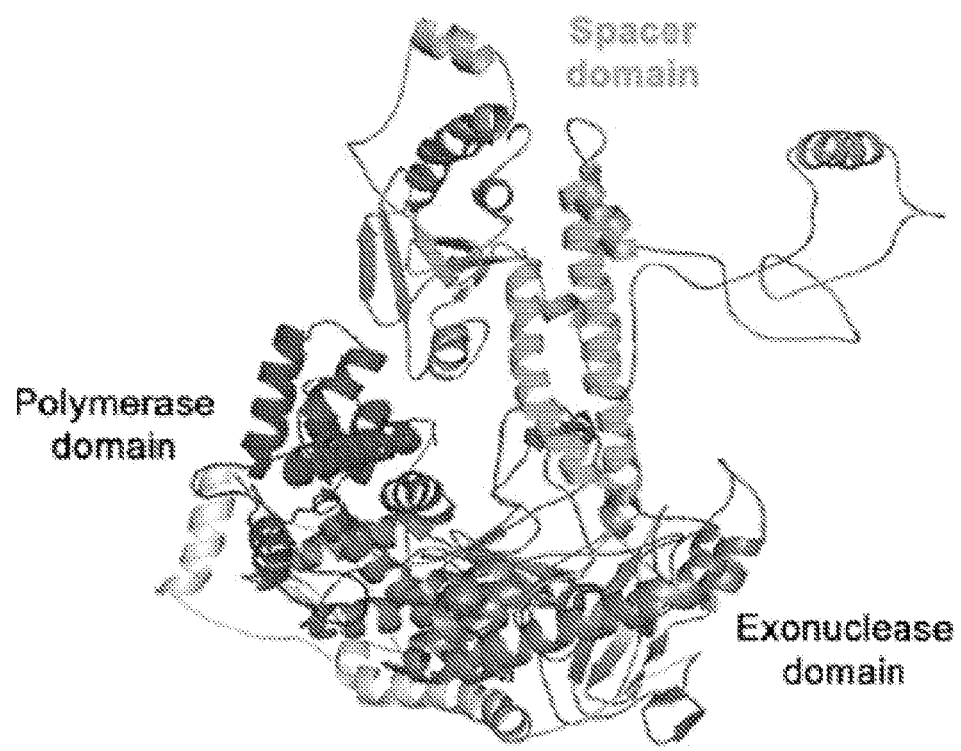
FIG. 5 provides a structure model of POLG.

It is to be appreciated that certain aspects, modes, embodiments, variations and features of the invention are described below in various levels of detail in order to provide a substantial understanding of the present invention. The definitions of certain terms as used in this specification are provided below. Unless defined otherwise, all technical and scientific terms used herein generally have the same meaning as commonly understood by one of ordinary skill in the art to which this invention belongs.

In practicing the present invention, many conventional techniques in molecular biology, protein biochemistry, cell biology, immunology, microbiology and recombinant DNA are used. These techniques are well-known and are explained in, e.g., *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y., 1989); *DNA Cloning: A Practical Approach*, Vols. I and II, Glover, Ed. (1985); *Oligonucleotide Synthesis*, Gait, Ed. (1984); *Nucleic Acid Hybridization*, Hames & Higgins, Eds. (1985); *Transcription and Translation*, Hames & Higgins, Eds. (1984); *Animal Cell Culture*, Freshney, Ed. (1986); *Immobilized Cells and Enzymes* (IRL Press, 1986); Perbal, *A Practical Guide to Molecular Cloning*; the series, *Meth. Enzymol.*, (Academic Press, Inc., 1984); *Gene Transfer Vectors for Mammalian Cells*, Miller & Calos, Eds. (Cold Spring Harbor Laboratory, N Y, 1987); and *Meth. Enzymol.*, Vols. 154 and 155, Wu & Grossman, and Wu, Eds., respectively.

As used in this specification and the appended claims, the singular forms "a", "an" and "the" include plural referents unless the content clearly dictates otherwise. For example, reference to "a cell" includes a combination of two or more cells, and the like.

As used herein, the "administration" of an agent, drug, or peptide to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. In some embodiments, the aromatic-cationic peptide is administered by an intracoronary route or an intra-arterial route. Administration includes self-administration and the administration by another.

As used herein, the term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission.

As used herein, the term "effective amount" refers to a quantity sufficient to achieve a desired therapeutic or prophylactic effect, e.g., an amount which results in the prevention or amelioration of a mitochondrial disease or disorder or symptoms thereof associated with mutations in the SURF1 gene or POLG gene or one or more symptoms associated with disruption of mitochondrial oxidative phosphorylation associated with mutations in the SURF1 gene or POLG gene. In the context of therapeutic applications, the amount of a composition administered to the subject will depend on the type and severity of the disease and on the characteristics of the individual, such as general health, age, sex, body weight and tolerance to drugs. It will also depend on the degree, severity and type of disease. The skilled artisan were able to determine appropriate dosages depending on these and other factors. The compositions can also be administered in combination with one or more additional therapeutic compounds. In the methods described herein, the aromatic-cationic peptides may be administered to a subject having one or more signs or symptoms of disruption of mitochondrial oxidative phosphorylation. For example, a "therapeutically effective amount" of the aromatic-cationic peptides is means levels in which the physiological effects of disruption of mitochondrial oxidative phosphorylation are, at a minimum, ameliorated.

As used herein, the terms "treating" or "treatment" or "alleviation" refers to therapeutic and prophylactic treatment and measures, wherein the object is to prevent or ameliorate or slow down (lessen) the targeted pathologic condition or disorder. For example, a subject is successfully "treated" for mitochondrial disease or disorder associated with mutations in the SURF1 gene or POLG gene if, after receiving a therapeutic amount of the aromatic-cationic peptides according to the methods described herein, the subject shows observable and/or measurable reduction in the disruption of mitochondrial oxidative phosphorylation. It is also to be appreciated that the various modes of treatment or prevention of medical conditions and/or their symptoms as described are intended to mean "substantial," which includes total but also less than total treatment and wherein some biologically or medically relevant result is achieved.

As used herein, "prevention" or "preventing" of a disorder or condition refers to a compound that, in a statistical sample, reduces the occurrence of symptoms of a disorder or condition in the treated sample relative to an untreated control sample, or delays the onset or reduces the severity of one or more symptoms of the disorder or condition relative to the untreated control sample. As used herein, preventing mitochondrial disease or disorder associated with mutations in the SURF1 gene or POLG gene includes preventing oxidative damage or preventing mitochondrial permeability transitioning, thereby preventing or ameliorating the harmful effects of the disruption of mitochondrial oxidative phosphorylation.

An "isolated" or "purified" polypeptide or peptide is substantially free of cellular material or other contaminating polypeptides from the cell or tissue source from which the agent is derived, or substantially free from chemical precursors or other chemicals when chemically synthesized. For example, an isolated aromatic-cationic peptide would be free of materials that would interfere with diagnostic or therapeutic uses of the agent. Such interfering materials may include enzymes, hormones and other proteinaceous and nonproteinaceous solutes.

As used herein, the terms "polypeptide," "peptide," and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art.

As used herein, the term "simultaneous" therapeutic use refers to the administration of at least two active ingredients by the same route and at the same time or at substantially the same time.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

Mutations Associated with Mitochondrial Diseases
SURF1

Oxidative phosphorylation (OXPHOS) is involved in cellular function as the primary source for energy (ATP) in most cell types, the control point for cellular redox, and as a control point for essential metabolic and signaling pathways that range from the synthesis of pyrimidines to the regulation of apoptosis. Optimal OXPHOS function requires aggregation of individual OXPHOS enzymes into supercomplexes which allows efficient and rapid transport of electrons. Supercomplexes allow efficient formation of an electrochemical (proton) gradient created by Complexes I, III, and IV that is then used by Complex V to synthesize ATP. In many classes of mitochondrial disease, impairment of the monomeric enzymes (Complexes I-V) and supercomplex assembly occurs. Functional supercomplexes contain a single Complex I enzyme, two Complex III enzymes, and variable numbers of Complex IV enzymes (Complexes I+III2+IV) plus the mobile electron carriers CoQ10 and cytochrome c. Complex II also can be associated with the Complex I+III2+IV structure. During isolation of supercomplexes, other classes of supercomplexes are observed: (1) Complexes I+III2+V; (2) Complexes I+III2+IV; (3) Complexes III+IV. The role of these other supercomplex classes, particularly those lacking Complex IV are unknown, but they may be intermediate structure involved in functional supercomplex assembly.

SURF1 is a 300 amino acid, nine exon nuclear gene that functions as an assembly factor for Complex IV (cytochrome c oxidase). Pathogenic mutations of the SURF1 gene typically result in profound Complex IV defects. The most frequently encountered mutations in the SURF1 gene are a common cause of Leigh syndrome. OXPHOS disease attributed to the SURF1 mutation are thought to be transmitted in an autosomal recessive fashion.

The effects of gene mutations involving Complex IV (cytochrome c oxidase) on supercomplex formation has been investigated in only a few cases harboring SURF1, COX10, and SCO1 mutations, (see Williams et al., *J. Biol. Chem.*, 279(9): 7462-69 (2004); Diaz et al., *Mol. Cell Biol.*, 26(13): 4872-81 (2006); Acin-Perez et al., *Mol. Cell*, 32(4): 529-39 (2008)). Mutations in SURF1, COX10 and SCO1, Complex IV assembly factors, may be recognized by the diffuse decrease in Complex IV activity observed by histochemical, immunofluorescence, enzymology, and protein chemistry approaches. To date, all patients with mutations in these genes show impaired assembly of supercomplexes.

Assessment of patients with SURF1 mutations demonstrates diverse effects on OXPHOS function. OXPHOS supercomplex analysis and monomeric enzyme analysis of mutated SURF1 showed the following features:
1) Decreased supercomplex formation of (A) Complexes I+III2; (B) Complexes I+III2+IV1; and (C) Complexes I+III2+IVn (n=2 or more).
2) Monomeric Complex IV is highly abnormal showing decreased assembly as well as abnormal high and low molecular weight Complex IV structures. These abnormal Complex IV structures likely represent abnormally assembled and dysfunctional Complex IV.

3) In severe cases, Complex V appears to be affected. When the whole Complex V (ATP synthase) enzyme is isolated for clear native in-gel enzymological analysis, patients can show impaired ATPase activity. This finding suggests that Complex V may be secondarily affected in some patients with SURF1 mutations, thus contributing to phenotypic variation observed among these patients.

POLG

The DNA polymerase gamma gene, POLG, encodes the catalytic subunit of DNA polymerase gamma, which is required for replication and repair of the mitochondrial DNA. Mutations in POLG and have been reported multiple times in the literature, and are correlated with numerous diseases and conditions, such as, for example progressive external ophthalmoplegia (PEO), Alpers' disease, and sensory ataxic neuropathy with dysarthria and ophthalmoparesis (SANDO), as both a homozygous mutation or as a compound heterozygous mutation with another mutation, (see *Nature Genetics,* 28(3):211-2 (2001); *Hum. Mol Genet.,* 17, 2496-2506 (2009); *J. Med. Genet.,* 46, 209-14 (2009); *J. Inhert. Metab. Dis.,* 32, 143-158 (2009); *Muscle Nerve,* 41(2); 265-9 (2010); *Neurology,* 73(11): 898-9003 (2009); *J. Med. Genet.,* 46(11):776-85 (2009)). The most severe manifestation of defects of the POLG protein have been associated with mutations of the 'spacer' region of POLG. This mutation is reported to disrupt subunit interaction and lower DNA binding and catalytic efficiency of polymerase.

Mitochondrial Diseases or Disorders

Leigh Syndrome

More than 40 different SURF1 gene mutations have been identified in patients with Leigh syndrome, a progressive brain disorder that usually appears in infancy or early childhood.

Approximately 10 to 15 percent of people with Leigh syndrome have a mutation in the SURF1 gene. Most SURF1 gene mutations result in an abnormally short SURF1 protein. Other mutations replace a single amino acid in the SURF1 protein. The mutated proteins are degraded in the cell, which results in the absence of SURF1 protein. As discussed above, mutations in SURF1 gene is associated with decreased OXPHOS function.

Alpers' Disease

Alpers' disease is a progressive, neurodevelopmental, mitochondrial DNA (mtDNA) depletion syndrome. Alpers' disease is an autosomal recessive disease caused by mutation in the gene for the mitochondrial DNA polymerase POLG. The disease occurs in about one in 100,000 persons. Most individuals with Alpers' disease do not show symptoms at birth and develop normally for weeks to years before the onset of symptoms. Diagnosis is established by testing for the POLG gene. Symptoms typically occur months before tissue samples show the mitochondrial DNA depletion. About 80 percent of individuals with Alpers' disease develop symptoms in the first two years of life, and 20 percent develop symptoms between ages 2 and 25.

Progressive External Ophthalmoplegia

Progressive external ophthalmoplegia (PEO) is a condition caused by defects in mitochondria. Affected individuals often have large deletions of genetic material from mitochondrial DNA (mtDNA) in muscle tissue. PEO can result from mutations in several different genes. In some cases, mutations in nuclear DNA are responsible for PEO, particularly mutations in the POLG genes. These genes are critical for mtDNA maintenance. Although the mechanism is unclear, mutations in any of these three genes lead to large deletions of mtDNA, ranging from 2,000 to 10,000 nucleotides.

POE typically appears in adults between ages 18 and 40. Signs and symptoms of progressive external ophthalmoplegia include, but are limited to, drooping eyelids (ptosis), which can affect one or both eyelids, weakness or paralysis of the muscles that move the eye (ophthalmoplegia), general weakness of the skeletal muscles (myopathy), particularly in the neck, arms, or legs, and difficulty swallowing (dysphagia).

Ataxia Neuropathy Spectrum

Ataxia neuropathy spectrum is part of a group of conditions called the POLG-related disorders. The conditions in this group feature a range of similar signs and symptoms involving muscle-, nerve-, and brain-related functions. Ataxia neuropathy spectrum includes the conditions called mitochondrial recessive ataxia syndrome (MIRAS) and sensory ataxia neuropathy dysarthria and ophthalmoplegia (SANDO).

Mutations in the POLG gene often result in fewer copies of mtDNA (mtDNA depletion) or deletions of large regions of mtDNA (mtDNA deletion). MtDNA depletion and/or mtDNA deletion can lead to a decrease in OXPHOS.

Patients with ataxia neuropathy spectrum generally have problems with coordination and balance (ataxia) and disturbances in nerve function (neuropathy). The neuropathy can be classified as sensory, motor, or a combination of the two. Sensory neuropathy causes numbness, tingling, or pain in the arms and legs, and motor neuropathy refers to disturbance in the nerves used for muscle movement.

Aromatic-Cationic Peptides

The present technology relates to preventing, treating or ameliorating the disruption of mitochondrial oxidative phosphorylation associated with mutations in the SURF1 gene or POLG gene in a subject in need thereof, by administering aromatic-cationic peptides as disclosed herein such as D-Arg-2',6'-Dmt-Lys-Phe-NH$_2$, or pharmaceutically acceptable salts thereof, such as acetate salt or trifluoroacetate salt. The present technology relates to the prevention, treatment or amelioration of mitochondrial disease or conditions or symptoms thereof, in mammals through administration of therapeutically effective amounts of aromatic-cationic peptides as disclosed herein, such as D-Arg-2',6'-Dmt-Lys-Phe-NH$_2$, or pharmaceutically acceptable salts thereof, such as acetate salt or trifluoroacetate salt, to subjects in need thereof.

The aromatic-cationic peptides are water-soluble and highly polar. Despite these properties, the peptides can readily penetrate cell membranes. The aromatic-cationic peptides typically include a minimum of three amino acids or a minimum of four amino acids, covalently joined by peptide bonds. The maximum number of amino acids present in the aromatic-cationic peptides is about twenty amino acids covalently joined by peptide bonds. Suitably, the maximum number of amino acids is about twelve, more preferably about nine, and most preferably about six.

The amino acids of the aromatic-cationic peptides can be any amino acid. As used herein, the term "amino acid" is used to refer to any organic molecule that contains at least one amino group and at least one carboxyl group. Typically, at least one amino group is at the a position relative to a carboxyl group. The amino acids may be naturally occurring. Naturally occurring amino acids include, for example, the twenty most common levorotatory (L) amino acids normally found in mammalian proteins, i.e., alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan, (Trp), tyrosine (Tyr), and valine (Val). Other naturally occurring amino acids include, for example, amino acids that are synthesized in metabolic processes not associated with protein synthesis. For example, the amino acids ornithine and citrulline are synthesized in mammalian metabolism during the production of urea. Another example of a naturally occurring amino acid includes hydroxyproline (Hyp).

The peptides optionally contain one or more non-naturally occurring amino acids. Optimally, the peptide has no amino acids that are naturally occurring. The non-naturally occurring amino acids may be levorotary (L-), dextrorotatory (D-), or mixtures thereof. Non-naturally occurring amino acids are those amino acids that typically are not synthesized in normal metabolic processes in living organisms, and do not naturally occur in proteins. In addition, the non-naturally occurring amino acids suitably are also not recognized by common proteases. The non-naturally occurring amino acid can be present at any position in the peptide. For example, the non-naturally occurring amino acid can be at the N-terminus, the C-terminus, or at any position between the N-terminus and the C-terminus.

The non-natural amino acids may, for example, comprise alkyl, aryl, or alkylaryl groups not found in natural amino acids. Some examples of non-natural alkyl amino acids include α-aminobutyric acid, β-aminobutyric acid, γ-aminobutyric acid, δ-aminovaleric acid, and ε-aminocaproic acid. Some examples of non-natural aryl amino acids include ortho-, meta-, and para-aminobenzoic acid. Some examples of non-natural alkylaryl amino acids include ortho-, meta-, and para-aminophenylacetic acid, and γ-phenyl-β-aminobutyric acid. Non-naturally occurring amino acids include derivatives of naturally occurring amino acids. The derivatives of naturally occurring amino acids may, for example, include the addition of one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include branched or unbranched $C_1$-$C_4$ alkyl, such as methyl, ethyl, n-propyl, isopropyl, butyl, isobutyl, or t-butyl, $C_1$-$C_4$ alkyloxy (i.e., alkoxy), amino, $C_1$-$C_4$ alkylamino and $C_1$-$C_4$ dialkylamino (e.g., methylamino, dimethylamino), nitro, hydroxyl, halo (i.e., fluoro, chloro, bromo, or iodo). Some specific examples of non-naturally occurring derivatives of naturally occurring amino acids include norvaline (Nva) and norleucine (Nle).

Another example of a modification of an amino acid in a peptide is the derivatization of a carboxyl group of an aspartic acid or a glutamic acid residue of the peptide. One example of derivatization is amidation with ammonia or with a primary or secondary amine, e.g. methylamine, ethylamine, dimethylamine or diethylamine. Another example of derivatization includes esterification with, for example, methyl or ethyl alcohol. Another such modification includes derivatization of an amino group of a lysine, arginine, or histidine residue. For example, such amino groups can be acylated. Some suitable acyl groups include, for example, a benzoyl group or an alkanoyl group comprising any of the $C_1$-$C_4$ alkyl groups mentioned above, such as an acetyl or propionyl group.

The non-naturally occurring amino acids are suitably resistant or insensitive to common proteases. Examples of non-naturally occurring amino acids that are resistant or insensitive to proteases include the dextrorotatory (D-) form of any of the above-mentioned naturally occurring L-amino acids, as well as L- and/or D- non-naturally occurring amino acids. The D-amino acids do not normally occur in proteins, although they are found in certain peptide antibiotics that are synthesized by means other than the normal ribosomal protein synthetic machinery of the cell. As used herein, the D-amino acids are considered to be non-naturally occurring amino acids.

In order to minimize protease sensitivity, the peptides should have less than five, preferably less than four, more preferably less than three, and most preferably, less than two contiguous L-amino acids recognized by common proteases, irrespective of whether the amino acids are naturally or non-naturally occurring. Optimally, the peptide has only D-amino acids, and no L-amino acids. If the peptide contains protease sensitive sequences of amino acids, at least one of the amino acids is preferably a non-naturally-occurring D-amino acid, thereby conferring protease resistance. An example of a protease sensitive sequence includes two or more contiguous basic amino acids that are readily cleaved by common proteases, such as endopeptidases and trypsin. Examples of basic amino acids include arginine, lysine and histidine.

The aromatic-cationic peptides should have a minimum number of net positive charges at physiological pH in comparison to the total number of amino acid residues in the peptide. The minimum number of net positive charges at physiological pH will be referred to below as ($p_m$). The total number of amino acid residues in the peptide will be referred to below as (r). The minimum number of net positive charges discussed below are all at physiological pH. The term "physiological pH" as used herein refers to the normal pH in the cells of the tissues and organs of the mammalian body. For instance, the physiological pH of a human is normally approximately 7.4, but normal physiological pH in mammals may be any pH from about 7.0 to about 7.8.

"Net charge" as used herein refers to the balance of the number of positive charges and the number of negative charges carried by the amino acids present in the peptide. In this specification, it is understood that net charges are measured at physiological pH. The naturally occurring amino acids that are positively charged at physiological pH include L-lysine, L-arginine, and L-histidine. The naturally occurring amino acids that are negatively charged at physiological pH include L-aspartic acid and L-glutamic acid.

Typically, a peptide has a positively charged N-terminal amino group and a negatively charged C-terminal carboxyl group. The charges cancel each other out at physiological pH. As an example of calculating net charge, the peptide Tyr-Arg-Phe-Lys-Glu-His-Trp-D-Arg has one negatively charged amino acid (i.e., Glu) and four positively charged amino acids (i.e., two Arg residues, one Lys, and one His). Therefore, the above peptide has a net positive charge of three.

In one embodiment, the aromatic-cationic peptides have a relationship between the minimum number of net positive charges at physiological pH ($p_m$) and the total number of amino acid residues (r) wherein $3p_m$ is the largest number that is less than or equal to r+1. In this embodiment, the relationship between the minimum number of net positive charges ($p_m$) and the total number of amino acid residues (r) is as follows:

TABLE 1

Amino acid number and net positive charges ($3p_m \leq p + 1$)

| | (r) | | | | | | | | | | | | | | | | | |
|---|---|---|---|---|---|---|---|---|---|---|---|---|---|---|---|---|---|---|
| | 3 | 4 | 5 | 6 | 7 | 8 | 9 | 10 | 11 | 12 | 13 | 14 | 15 | 16 | 17 | 18 | 19 | 20 |
| ($p_m$) | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of net positive charges ($p_m$) and the total number of amino acid residues (r) wherein $2p_m$ is the largest number that is less than or equal to r+1. In this embodiment, the relationship between the minimum number of net positive charges ($p_m$) and the total number of amino acid residues (r) is as follows:

TABLE 2

Amino acid number and net positive charges ($2p_m \leq p + 1$)

| | (r) | | | | | | | | | | | | | | | | | |
|---|---|---|---|---|---|---|---|---|---|---|---|---|---|---|---|---|---|---|
| | 3 | 4 | 5 | 6 | 7 | 8 | 9 | 10 | 11 | 12 | 13 | 14 | 15 | 16 | 17 | 18 | 19 | 20 |
| ($p_m$) | 2 | 2 | 3 | 3 | 4 | 4 | 5 | 5 | 6 | 6 | 7 | 7 | 8 | 8 | 9 | 9 | 10 | 10 |

In one embodiment, the minimum number of net positive charges ($p_m$) and the total number of amino acid residues (r) are equal. In another embodiment, the peptides have three or four amino acid residues and a minimum of one net positive charge, suitably, a minimum of two net positive charges and more preferably a minimum of three net positive charges.

It is also important that the aromatic-cationic peptides have a minimum number of aromatic groups in comparison to the total number of net positive charges ($p_t$). The minimum number of aromatic groups will be referred to below as (a). Naturally occurring amino acids that have an aromatic group include the amino acids histidine, tryptophan, tyrosine, and phenylalanine. For example, the hexapeptide Lys-Gln-Tyr-D-Arg-Phe-Trp has a net positive charge of two (contributed by the lysine and arginine residues) and three aromatic groups (contributed by tyrosine, phenylalanine and tryptophan residues).

The aromatic-cationic peptides should also have a relationship between the minimum number of aromatic groups (a) and the total number of net positive charges at physiological pH ($p_t$) wherein 3a is the largest number that is less than or equal to $p_t$+1, except that when $p_t$ is 1, a may also be 1. In this embodiment, the relationship between the minimum number of aromatic groups (a) and the total number of net positive charges ($p_t$) is as follows:

TABLE 3

Aromatic groups and net positive charges ($3a \leq p_t + 1$ or $a = p_t = 1$)

| | ($p_t$) | | | | | | | | | | | | | | | | | | |
|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| (a) | 1 | 1 | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of aromatic groups (a) and the total number of net positive charges ($p_t$) wherein 2a is the largest number that is less than or equal to $p_t+1$. In this embodiment, the relationship between the minimum number of aromatic amino acid residues (a) and the total number of net positive charges ($p_t$) is as follows:

TABLE 4

Aromatic groups and net positive charges ($2a \le p_t + 1$ or $a = p_t = 1$)

| ($p_t$) | | | | | | | | | | | | | | | | | | | |
|---|---|---|---|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 | 16 | 17 | 18 | 19 | 20 |

| (a) | | | | | | | | | | | | | | | | | | | |
|---|---|---|---|---|---|---|---|---|---|---|---|---|---|---|---|---|---|---|---|
| 1 | 1 | 2 | 2 | 3 | 3 | 4 | 4 | 5 | 5 | 6 | 6 | 7 | 7 | 8 | 8 | 9 | 9 | 10 | 10 |

In another embodiment, the number of aromatic groups (a) and the total number of net positive charges ($p_t$) are equal.

Carboxyl groups, especially the terminal carboxyl group of a C-terminal amino acid, are suitably amidated with, for example, ammonia to form the C-terminal amide. Alternatively, the terminal carboxyl group of the C-terminal amino acid may be amidated with any primary or secondary amine. The primary or secondary amine may, for example, be an alkyl, especially a branched or unbranched $C_1$-$C_4$ alkyl, or an aryl amine.

Accordingly, the amino acid at the C-terminus of the peptide may be converted to an amido, N-methylamido, N-ethylamido, N,N-dimethylamido, N,N-diethylamido, N-methyl-N-ethylamido, N-phenylamido or N-phenyl-N-ethylamido group. The free carboxylate groups of the asparagine, glutamine, aspartic acid, and glutamic acid residues not occurring at the C-terminus of the aromatic-cationic peptides may also be amidated wherever they occur within the peptide. The amidation at these internal positions may be with ammonia or any of the primary or secondary amines described above.

In one embodiment, the aromatic-cationic peptide is a tripeptide having two net positive charges and at least one aromatic amino acid. In a particular embodiment, the aromatic-cationic peptide is a tripeptide having two net positive charges and two aromatic amino acids.

Aromatic-cationic peptides include, but are not limited to, the following peptide examples:

TABLE 5

EXEMPLARY PEPTIDES

2',6'-Dmp-D-Arg-2',6'-Dmt-Lys-NH$_2$

2',6'-Dmp-D-Arg-Phe-Lys-NH$_2$

2',6'-Dmt-D-Arg-PheOrn-NH$_2$

2',6'-Dmt-D-Arg-Phe-Ahp(2-aminoheptanoicacid)-NH$_2$

2',6'-Dmt-D-Arg-Phe-Lys-NH$_2$

2',6'-Dmt-D-Cit-PheLys-NH$_2$

Ala-D-Phe-D-Arg-Tyr-Lys-D-Trp-His-D-Tyr-Gly-Phe

Arg-D-Leu-D-Tyr-Phe-Lys-Glu-D-Lys-Arg-D-Trp-Lys-D-Phe-Tyr-D-Arg-Gly

Asp-Arg-D-Phe-Cys-Phe-D-Arg-D-Lys-Tyr-Arg-D-Tyr-Trp-D-His-D-Phe-Lys-Phe

Asp-D-Trp-Lys-Tyr-D-His-Phe-Arg-D-Gly-Lys-NH$_2$

D-Arg-2',6'-Dmt-Lys-Phe-NH$_2$

D-Glu-Asp-Lys-D-Arg-D-His-Phe-Phe-D-Val-Tyr-Arg-Tyr-D-Tyr-Arg-His-Phe-NH$_2$

D-His-Glu-Lys-Tyr-D-Phe-Arg

D-His-Lys-Tyr-D-Phe-Glu-D-Asp-D-Asp-D-His-D-Lys-Arg-Trp-NH$_2$

D-Tyr-Trp-Lys-NH$_2$

Glu-Arg-D-Lys-Tyr-D-Val-Phe-D-His-Trp-Arg-D-Gly-Tyr-Arg-D-Met-NH$_2$

Gly-Ala-Lys-Phe-D-Lys-Glu-Arg-Tyr-His-D-Arg-D-Arg-Asp-Tyr-Trp-D-His-Trp-His-D-Lys-Asp.

Gly-D-Phe-Lys-His-D-Arg-Tyr-NH$_2$

His-Tyr-D-Arg-Trp-Lys-Phe-D-Asp-Ala-Arg-Cys-D-Tyr-His-Phe-D-Lys-Tyr-His-Ser-NH$_2$

TABLE 5-continued

EXEMPLARY PEPTIDES

Lys-D-Arg-Tyr-NH$_2$

Lys-D-Gln-Tyr-Arg-D-Phe-Trp-NH$_2$

Lys-Trp-D-Tyr-Arg-Asn-Phe-Tyr-D-His-NH$_2$

Met-Tyr-D-Arg-Phe-Arg-NH$_2$

Met-Tyr-D-Lys-Phe-Arg

Phe-Arg-D-His-Asp

Phe-D-Arg-2',6'-Dmt-Lys-NH$_2$

Phe-D-Arg-His

Phe-D-Arg-Lys-Trp-Tyr-D-Arg-His

Phe-D-Arg-Phe-Lys-NH$_2$

Phe-Phe-D-Tyr-Arg-Glu-Asp-D-Lys-Arg-D-Arg-His-Phe-NH$_2$

Phe-Tyr-Lys-D-Arg-Trp-His-D-Lys-D-Lys-Glu-Arg-D-Tyr-Thr

Thr-Gly-Tyr-Arg-D-His-Phe-Trp-D-His-Lys

Thr-Tyr-Arg-D-Lys-Trp-Tyr-Glu-Asp-D-Lys-D-Arg-His-Phe-D-Tyr-Gly-Val-Ile-D-His-Arg-Tyr-Lys-NH$_2$

Trp-D-Lys-Tyr-Arg-NH$_2$

Trp-Lys-Phe-D-Asp-Arg-Tyr-D-His-Lys

Tyr-Asp-D-Lys-Tyr-Phe-D-Lys-D-Arg-Phe-Pro-D-Tyr-His-Lys

Tyr-D-Arg-Phe-Lys-Glu-NH$_2$

Tyr-D-Arg-Phe-Lys-NH$_2$

Tyr-D-His-Phe-D-Arg-Asp-Lys-D-Arg-His-Trp-D-His-Phe

Tyr-His-D-Gly-Met

Val-D-Lys-His-Tyr-D-Phe-Ser-Tyr-Arg-NH$_2$

---

In one embodiment, the peptides have mu-opioid receptor agonist activity (i.e., they activate the mu-opioid receptor). Peptides which have mu-opioid receptor agonist activity are typically those peptides which have a tyrosine residue or a tyrosine derivative at the N-terminus (i.e., the first amino acid position). Suitable derivatives of tyrosine include 2'-methyltyrosine (Mmt); 2',6'-dimethyltyrosine (2'6'-Dmt); 3',5'-dimethyltyrosine (3'5'Dmt); N, 2',6'-trimethyltyrosine (Tmt); and 2'-hydroxy-6'-methyltryosine (Hmt).

In one embodiment, a peptide that has mu-opioid receptor agonist activity has the formula Tyr-D-Arg-Phe-Lys-NH$_2$. Tyr-D-Arg-Phe-Lys-NH$_2$ has a net positive charge of three, contributed by the amino acids tyrosine, arginine, and lysine and has two aromatic groups contributed by the amino acids phenylalanine and tyrosine. The tyrosine of Tyr-D-Arg-Phe-Lys-NH$_2$ can be a modified derivative of tyrosine such as in 2',6'-dimethyltyrosine to produce the compound having the formula 2',6'-Dmt-D-Arg-Phe-Lys-NH$_2$. 2',6'-Dmt-D-Arg-Phe-Lys-NH$_2$ has a molecular weight of 640 and carries a net three positive charge at physiological pH. 2',6'-Dmt-D-Arg-Phe-Lys-NH$_2$ readily penetrates the plasma membrane of several mammalian cell types in an energy-independent manner (Zhao et al., *J. Pharmacol Exp Ther.*, 304:425-432, 2003).

Alternatively, in other instances, the aromatic-cationic peptide does not have mu-opioid receptor agonist activity. For example, during long-term treatment, such as in a chronic disease state or condition, the use of an aromatic-cationic peptide that activates the mu-opioid receptor may be contraindicated. In these instances, the potentially adverse or addictive effects of the aromatic-cationic peptide may preclude the use of an aromatic-cationic peptide that activates the mu-opioid receptor in the treatment regimen of a human patient or other mammal. Potential adverse effects may include sedation, constipation and respiratory depression. In such instances an aromatic-cationic peptide that does not activate the mu-opioid receptor may be an appropriate treatment. Peptides that do not have mu-opioid receptor agonist activity generally do not have a tyrosine residue or a derivative of tyrosine at the N-terminus (i.e., amino acid position 1). The amino acid at the N-terminus can be any naturally occurring or non-naturally occurring amino acid other than tyrosine. In one embodiment, the amino acid at the N-terminus is phenylalanine or its derivative. Exemplary derivatives of phenylalanine include 2'-methylphenylalanine (Mmp), 2',6'-dimethylphenylalanine (2',6'-Dmp), N, 2',6'-trimethylphenylalanine (Tmp), and 2'-hydroxy-6'-methylphenylalanine (Hmp).

An example of an aromatic-cationic peptide that does not have mu-opioid receptor agonist activity has the formula Phe-D-Arg-Phe-Lys-NH$_2$. Alternatively, the N-terminal phenylalanine can be a derivative of phenylalanine such as 2',6'-dimethylphenylalanine (2'6'-Dmp). In one embodiment, the amino acid sequence of 2',6'-Dmt-D-Arg-Phe-Lys-NH$_2$ is rearranged such that Dmt is not at the N-terminus. An example of such an aromatic-cationic peptide that does not have mu-opioid receptor agonist activity has the formula D-Arg-2'6'-Dmt-Lys-Phe-NH$_2$.

Suitable substitution variants of the peptides listed herein include conservative amino acid substitutions. Amino acids may be grouped according to their physicochemical characteristics as follows:

(a) Non-polar amino acids: Ala(A) Ser(S) Thr(T) Pro(P) Gly(G) Cys (C);

(b) Acidic amino acids: Asn(N) Asp(D) Glu(E) Gln(Q);

(c) Basic amino acids: His(H) Arg(R) Lys(K);

(d) Hydrophobic amino acids: Met(M) Leu(L) Ile(I) Val (V); and (e) Aromatic amino acids: Phe (F) Tyr(Y) Trp (W) His (H).

Substitutions of an amino acid in a peptide by another amino acid in the same group is referred to as a conservative substitution and may preserve the physicochemical characteristics of the original peptide. In contrast, substitutions of an amino acid in a peptide by another amino acid in a different group are generally more likely to alter the characteristics of the original peptide.

Examples of peptides that activate mu-opioid receptors include, but are not limited to, the aromatic-cationic peptides shown in Table 6.

TABLE 6

Peptide Analogs with Mu-Opioid Activity

| Amino Acid Position 1 | Amino Acid Position 2 | Amino Acid Position 3 | Amino Acid Position 4 | C-Terminal Modification |
|---|---|---|---|---|
| Tyr | D-Arg | Phe | Lys | NH$_2$ |
| Tyr | D-Arg | Phe | Orn | NH$_2$ |
| Tyr | D-Arg | Phe | Dab | NH$_2$ |
| Tyr | D-Arg | Phe | Dap | NH$_2$ |
| 2'6'Dmt | D-Arg | Phe | Lys | NH$_2$ |
| 2'6'Dmt | D-Arg | Phe | Lys-NH(CH$_2$)$_2$—NH-dns | NH$_2$ |
| 2'6'Dmt | D-Arg | Phe | Lys-NH(CH$_2$)$_2$—NH-atn | NH$_2$ |
| 2'6'Dmt | D-Arg | Phe | dnsLys | NH$_2$ |
| 2'6'Dmt | D-Cit | Phe | Lys | NH$_2$ |
| 2'6'Dmt | D-Cit | Phe | Ahp | NH$_2$ |
| 2'6'Dmt | D-Arg | Phe | Orn | NH$_2$ |
| 2'6'Dmt | D-Arg | Phe | Dab | NH$_2$ |
| 2'6'Dmt | D-Arg | Phe | Dap | NH$_2$ |
| 2'6'Dmt | D-Arg | Phe | Ahp(2-aminoheptanoic acid) | NH$_2$ |
| Bio-2'6'Dmt | D-Arg | Phe | Lys | NH$_2$ |
| 3'5'Dmt | D-Arg | Phe | Lys | NH$_2$ |
| 3'5'Dmt | D-Arg | Phe | Orn | NH$_2$ |
| 3'5'Dmt | D-Arg | Phe | Dab | NH$_2$ |
| 3'5'Dmt | D-Arg | Phe | Dap | NH$_2$ |
| Tyr | D-Arg | Tyr | Lys | NH$_2$ |
| Tyr | D-Arg | Tyr | Orn | NH$_2$ |
| Tyr | D-Arg | Tyr | Dab | NH$_2$ |
| Tyr | D-Arg | Tyr | Dap | NH$_2$ |
| 2'6'Dmt | D-Arg | Tyr | Lys | NH$_2$ |
| 2'6'Dmt | D-Arg | Tyr | Orn | NH$_2$ |
| 2'6'Dmt | D-Arg | Tyr | Dab | NH$_2$ |
| 2'6'Dmt | D-Arg | Tyr | Dap | NH$_2$ |
| 2'6'Dmt | D-Arg | 2'6'Dmt | Lys | NH$_2$ |
| 2'6'Dmt | D-Arg | 2'6'Dmt | Orn | NH$_2$ |
| 2'6'Dmt | D-Arg | 2'6'Dmt | Dab | NH$_2$ |
| 2'6'Dmt | D-Arg | 2'6'Dmt | Dap | NH$_2$ |
| 3'5'Dmt | D-Arg | 3'5'Dmt | Arg | NH$_2$ |
| 3'5'Dmt | D-Arg | 3'5'Dmt | Lys | NH$_2$ |
| 3'5'Dmt | D-Arg | 3'5'Dmt | Orn | NH$_2$ |
| 3'5'Dmt | D-Arg | 3'5'Dmt | Dab | NH$_2$ |
| Tyr | D-Lys | Phe | Dap | NH$_2$ |
| Tyr | D-Lys | Phe | Arg | NH$_2$ |
| Tyr | D-Lys | Phe | Lys | NH$_2$ |
| Tyr | D-Lys | Phe | Orn | NH$_2$ |
| 2'6'Dmt | D-Lys | Phe | Dab | NH$_2$ |
| 2'6'Dmt | D-Lys | Phe | Dap | NH$_2$ |
| 2'6'Dmt | D-Lys | Phe | Arg | NH$_2$ |
| 2'6'Dmt | D-Lys | Phe | Lys | NH$_2$ |
| 3'5'Dmt | D-Lys | Phe | Orn | NH$_2$ |
| 3'5'Dmt | D-Lys | Phe | Dab | NH$_2$ |
| 3'5'Dmt | D-Lys | Phe | Dap | NH$_2$ |
| 3'5'Dmt | D-Lys | Phe | Arg | NH$_2$ |
| Tyr | D-Lys | Tyr | Lys | NH$_2$ |
| Tyr | D-Lys | Tyr | Orn | NH$_2$ |
| Tyr | D-Lys | Tyr | Dab | NH$_2$ |
| Tyr | D-Lys | Tyr | Dap | NH$_2$ |
| 2'6'Dmt | D-Lys | Tyr | Lys | NH$_2$ |
| 2'6'Dmt | D-Lys | Tyr | Orn | NH$_2$ |
| 2'6'Dmt | D-Lys | Tyr | Dab | NH$_2$ |
| 2'6'Dmt | D-Lys | Tyr | Dap | NH$_2$ |
| 2'6'Dmt | D-Lys | 2'6'Dmt | Lys | NH$_2$ |
| 2'6'Dmt | D-Lys | 2'6'Dmt | Orn | NH$_2$ |
| 2'6'Dmt | D-Lys | 2'6'Dmt | Dab | NH$_2$ |
| 2'6'Dmt | D-Lys | 2'6'Dmt | Dap | NH$_2$ |
| 2'6'Dmt | D-Arg | Phe | dnsDap | NH$_2$ |
| 2'6'Dmt | D-Arg | Phe | atnDap | NH$_2$ |
| 3'5'Dmt | D-Lys | 3'5'Dmt | Lys | NH$_2$ |
| 3'5'Dmt | D-Lys | 3'5'Dmt | Orn | NH$_2$ |
| 3'5'Dmt | D-Lys | 3'5'Dmt | Dab | NH$_2$ |
| 3'5'Dmt | D-Lys | 3'5'Dmt | Dap | NH$_2$ |
| Tyr | D-Lys | Phe | Arg | NH$_2$ |
| Tyr | D-Orn | Phe | Arg | NH$_2$ |
| Tyr | D-Dab | Phe | Arg | NH$_2$ |
| Tyr | D-Dap | Phe | Arg | NH$_2$ |
| 2'6'Dmt | D-Arg | Phe | Arg | NH$_2$ |
| 2'6'Dmt | D-Lys | Phe | Arg | NH$_2$ |
| 2'6'Dmt | D-Orn | Phe | Arg | NH$_2$ |
| 2'6'Dmt | D-Dab | Phe | Arg | NH$_2$ |
| 3'5'Dmt | D-Dap | Phe | Arg | NH$_2$ |
| 3'5'Dmt | D-Arg | Phe | Arg | NH$_2$ |
| 3'5'Dmt | D-Lys | Phe | Arg | NH$_2$ |
| 3'5'Dmt | D-Orn | Phe | Arg | NH$_2$ |
| Tyr | D-Lys | Tyr | Arg | NH$_2$ |
| Tyr | D-Orn | Tyr | Arg | NH$_2$ |
| Tyr | D-Dab | Tyr | Arg | NH$_2$ |
| Tyr | D-Dap | Tyr | Arg | NH$_2$ |
| 2'6'Dmt | D-Arg | 2'6'Dmt | Arg | NH$_2$ |
| 2'6'Dmt | D-Lys | 2'6'Dmt | Arg | NH$_2$ |
| 2'6'Dmt | D-Orn | 2'6'Dmt | Arg | NH$_2$ |
| 2'6'Dmt | D-Dab | 2'6'Dmt | Arg | NH$_2$ |
| 3'5'Dmt | D-Dap | 3'5'Dmt | Arg | NH$_2$ |
| 3'5'Dmt | D-Arg | 3'5'Dmt | Arg | NH$_2$ |
| 3'5'Dmt | D-Lys | 3'5'Dmt | Arg | NH$_2$ |
| 3'5'Dmt | D-Orn | 3'5'Dmt | Arg | NH$_2$ |
| Mmt | D-Arg | Phe | Lys | NH$_2$ |
| Mmt | D-Arg | Phe | Orn | NH$_2$ |
| Mmt | D-Arg | Phe | Dab | NH$_2$ |
| Mmt | D-Arg | Phe | Dap | NH$_2$ |
| Tmt | D-Arg | Phe | Lys | NH$_2$ |
| Tmt | D-Arg | Phe | Orn | NH$_2$ |
| Tmt | D-Arg | Phe | Dab | NH$_2$ |
| Tmt | D-Arg | Phe | Dap | NH$_2$ |
| Hmt | D-Arg | Phe | Lys | NH$_2$ |
| Hmt | D-Arg | Phe | Orn | NH$_2$ |
| Hmt | D-Arg | Phe | Dab | NH$_2$ |
| Hmt | D-Arg | Phe | Dap | NH$_2$ |
| Mmt | D-Lys | Phe | Lys | NH$_2$ |
| Mmt | D-Lys | Phe | Orn | NH$_2$ |
| Mmt | D-Lys | Phe | Dab | NH$_2$ |
| Mmt | D-Lys | Phe | Dap | NH$_2$ |
| Mmt | D-Lys | Phe | Arg | NH$_2$ |
| Tmt | D-Lys | Phe | Lys | NH$_2$ |

TABLE 6-continued

Peptide Analogs with Mu-Opioid Activity

| Amino Acid Position 1 | Amino Acid Position 2 | Amino Acid Position 3 | Amino Acid Position 4 | C-Terminal Modification |
|---|---|---|---|---|
| Tmt | D-Lys | Phe | Orn | $NH_2$ |
| Tmt | D-Lys | Phe | Dab | $NH_2$ |
| Tmt | D-Lys | Phe | Dap | $NH_2$ |
| Tmt | D-Lys | Phe | Arg | $NH_2$ |
| Hmt | D-Lys | Phe | Lys | $NH_2$ |
| Hmt | D-Lys | Phe | Orn | $NH_2$ |
| Hmt | D-Lys | Phe | Dab | $NH_2$ |
| Hmt | D-Lys | Phe | Dap | $NH_2$ |
| Hmt | D-Lys | Phe | Arg | $NH_2$ |
| Mmt | D-Lys | Phe | Arg | $NH_2$ |
| Mmt | D-Orn | Phe | Arg | $NH_2$ |
| Mmt | D-Dab | Phe | Arg | $NH_2$ |
| Mmt | D-Dap | Phe | Arg | $NH_2$ |
| Mmt | D-Arg | Phe | Arg | $NH_2$ |
| Tmt | D-Lys | Phe | Arg | $NH_2$ |
| Tmt | D-Orn | Phe | Arg | $NH_2$ |
| Tmt | D-Dab | Phe | Arg | $NH_2$ |
| Tmt | D-Dap | Phe | Arg | $NH_2$ |
| Tmt | D-Arg | Phe | Arg | $NH_2$ |
| Hmt | D-Lys | Phe | Arg | $NH_2$ |
| Hmt | D-Orn | Phe | Arg | $NH_2$ |
| Hmt | D-Dab | Phe | Arg | $NH_2$ |
| Hmt | D-Dap | Phe | Arg | $NH_2$ |
| Hmt | D-Arg | Phe | Arg | $NH_2$ |

Dab = diaminobutyric
Dap = diaminopropionic acid
Dmt = dimethyltyrosine
Mmt = 2'-methyltyrosine
Tmt = N,2',6'-trimethyltyrosine
Hmt = 2'-hydroxy,6'-methyltyrosine
dnsDap = β-dansyl-L-α,β-diaminopropionic acid
atnDap = β-anthraniloyl-L-α,β-diaminopropionic acid
Bio = biotin Examples of peptides that do not activate mu-opioid receptors include, but are not limited to, the aromatic-cationic peptides shown in Table 7.

TABLE 7

Peptide Analogs Lacking Mu-Opioid Activity

| Amino Acid Position 1 | Amino Acid Position 2 | Amino Acid Position 3 | Amino Acid Position 4 | C-Terminal Modification |
|---|---|---|---|---|
| D-Arg | Dmt | Lys | Phe | $NH_2$ |
| D-Arg | Dmt | Phe | Lys | $NH_2$ |
| D-Arg | Phe | Lys | Dmt | $NH_2$ |
| D-Arg | Phe | Dmt | Lys | $NH_2$ |
| D-Arg | Lys | Dmt | Phe | $NH_2$ |
| D-Arg | Lys | Phe | Dmt | $NH_2$ |
| Phe | Lys | Dmt | D-Arg | $NH_2$ |
| Phe | Lys | D-Arg | Dmt | $NH_2$ |
| Phe | D-Arg | Phe | Lys | $NH_2$ |
| Phe | D-Arg | Dmt | Lys | $NH_2$ |
| Phe | D-Arg | Lys | Dmt | $NH_2$ |
| Phe | Dmt | D-Arg | Lys | $NH_2$ |
| Phe | Dmt | Lys | D-Arg | $NH_2$ |
| Lys | Phe | D-Arg | Dmt | $NH_2$ |
| Lys | Phe | Dmt | D-Arg | $NH_2$ |
| Lys | Dmt | D-Arg | Phe | $NH_2$ |
| Lys | Dmt | Phe | D-Arg | $NH_2$ |
| Lys | D-Arg | Phe | Dmt | $NH_2$ |
| Lys | D-Arg | Dmt | Phe | $NH_2$ |
| D-Arg | Dmt | D-Arg | Phe | $NH_2$ |
| D-Arg | Dmt | D-Arg | Dmt | $NH_2$ |
| D-Arg | Dmt | D-Arg | Tyr | $NH_2$ |
| D-Arg | Dmt | D-Arg | Trp | $NH_2$ |
| Trp | D-Arg | Phe | Lys | $NH_2$ |
| Trp | D-Arg | Tyr | Lys | $NH_2$ |
| Trp | D-Arg | Trp | Lys | $NH_2$ |
| Trp | D-Arg | Dmt | Lys | $NH_2$ |
| D-Arg | Trp | Lys | Phe | $NH_2$ |
| D-Arg | Trp | Phe | Lys | $NH_2$ |
| D-Arg | Trp | Lys | Dmt | $NH_2$ |
| D-Arg | Trp | Dmt | Lys | $NH_2$ |
| D-Arg | Lys | Trp | Phe | $NH_2$ |
| D-Arg | Lys | Trp | Dmt | $NH_2$ |
| Cha | D-Arg | Phe | Lys | $NH_2$ |
| Ala | D-Arg | Phe | Lys | $NH_2$ |

Cha = cyclohexyl alanine

The amino acids of the peptides shown in Table may be in either the L- or the D-configuration.

The peptides may be synthesized by any of the methods well known in the art. Suitable methods for chemically synthesizing the protein include, for example, those described by Stuart and Young in *Solid Phase Peptide Synthesis*, Second Edition, Pierce Chemical Company (1984), and in *Methods Enzymol.*, 289, Academic Press, Inc., New York (1997).

Therapeutic Uses of Aromatic-Cationic Peptides.

General.

The aromatic-cationic peptides described herein such as D-Arg-2',6'-Dmt-Lys-Phe-$NH_2$, or pharmaceutically acceptable salts thereof, such as acetate salt or trifluoroacetate salt, are useful to prevent or treat mitochondrial disease associated with mutations in the SURF1 gene or POLG gene or symptoms thereof. Specifically, the disclosure provides for both prophylactic and therapeutic methods of treating a subject having or suspected of having a mitochondrial disease, condition or disorder associated with mutations in the SURF1 gene or POLG gene. For example, in some embodiments, the disclosure provides for both prophylactic and therapeutic methods of treating a subject having a disruption in oxidative phosphorylation cause by a gene mutation in SURF1 or POLG. Accordingly, the present methods provide for the treatment or prevention of mitochondrial disease or disorder or symptoms thereof associated with mutations in the SURF1 gene or POLG gene in a subject by administering an effective amount of an aromatic-cationic peptide to a subject in need thereof to reduce disruption in oxidative phosphorylation of the subject. The present technology relates to the prevention, treatment or amelioration of mitochondrial disease or conditions or mitochondrial dysfunction or symptoms thereof associated with mutations in the SURF1 gene or POLG gene in mammals through administration of therapeutically effective amounts of aromatic-cationic peptides as disclosed herein, such as D-Arg-2',6'-Dmt-Lys-Phe-$NH_2$, or pharmaceutically acceptable salts thereof, such as acetate salt or trifluoroacetate salt, to subjects in need thereof.

In some embodiments, disruption in oxidative phosphorylation is determined by assays well known in the art. By way of example, but not by way of limitation, a disruption in oxidative phosphorylation is determined by assays that measures levels of coenzyme $Q_{10}$ (COQ10). In some embodiments, disruption in oxidative phosphorylation is determined by assays that measure OXPHOS capacity by the uncoupling ratio. In some embodiments, disruption in oxidative phosphorylation is determined by assays that measure the net routine flux control ratio. In some embodiments, disruption in oxidative phosphorylation is determined by assays that measure leak flux control ratio. In some embodiments, disruption in oxidative phosphorylation is determined by assays that measure the phosphorylation respiratory control ratio.

Uncoupling ratio (UCR) is an expression of the respiratory reserve capacity and indicates the OXPHOS capacity of the cells. In some embodiments, UCR is defined as $Cr_u/Cr$. $Cr_u$ is the maximum rate of oxygen utilization (Oxygen flux) produced when mitochondria are chemically uncoupled using FCCP (Carbonyl cyanide 4-(trifluoromethoxy) phenylhydrazone). FCCP titration must be performed since the concentration of FCCP required to produce maximum oxygen utilization varies among different cell lines. Once the maximum oxygen utilization is reached, further increases in FCCP inhibit oxygen utilization by oxidative phosphorylation. In some embodiments, Cr represents oxygen utilization by the cells during a normal cellular respiration with excess substrates.

In some embodiments, the Net Routine Flux Control Ratio ($Cr/Cr_u$) is the inverse of the UCR. In some embodiments, this value assesses how close routine respiration operate to the respiratory capacity of oxidative phosphorylation.

In some embodiments, the Respiratory Control Ratio (RCR) is defined as $Cr_u/Cr_o$. $Cr_u$ is defined above. $Cr_o$=Respiration after inhibition of Complex V (ATP synthase) by oligomycin. In some embodiments, this ratio allows assessment of uncoupling and OXPHOS dysfunction.

In some embodiments, the Leak Flux Control Ratio is determined by $Cr_o/Cr_u$. In some embodiments, this parameter is the inverse of RCR and represent proton leak with inhibition of ADP phosphorylation by oligomycin.

In some embodiments, the Phosphorylation Respiratory Control Ratio (RCRp) is defined as $(Cr-Cr_o)/Cr_u$ (or 1/UCR−1/RCR). In some embodiments, the RCRp is an index which expresses phosphorylation-related respiration ($Cr-Cr_o$) as a function of respiratory capacity ($Cr_u$). In some embodiments, the RCRp remains constant, if partial uncoupling is fully compensated by an increased routine respiration rate and a constant rate of oxidative phosphorylation is maintained. In some embodiments, the respiratory capacity declines without effect on the rate of oxidative phosphorylation; in some embodiments, the RCRp increases, which indicates that a higher proportion of the maximum capacity is activated to drive ATP synthesis. In some embodiments, the RCRp declines to zero in either fully uncoupled cells or in cells under complete metabolic arrest.

Accordingly, in some embodiments, therapeutic prevention of symptoms and/or treatment of subjects having mitochondrial disorder or disease associated with mutations in the SURF1 gene or POLG gene, with an aromatic cationic peptide as disclosed herein, such as D-Arg-2',6'Dmt-Lys-Phe-NH$_2$ (SS-31) or a pharmaceutically acceptable salt thereof, such as acetate or trifluoroacetate salt will reduce the disruption in oxidative phosphorylation, thereby ameliorating or preventing symptoms of mitochondrial diseases and disorders associated with mutations in the SURF1 gene or POLG gene. Symptoms of mitochondrial diseases or disorders associated with mutations in the SURF1 gene or POLG gene include, but are not limited to, poor growth, loss of muscle coordination, muscle weakness, neurological deficit, seizures, autism, autistic spectrum, autistic-like features, learning disabilities, heart disease, liver disease, kidney disease, gastrointestinal disorders, severe constipation, diabetes, increased risk of infection, thyroid dysfunction, adrenal dysfunction, autonomic dysfunction, confusion, disorientation, memory loss, poor growth, failure to thrive, poor coordination, sensory (vision, hearing) problems, reduced mental functions, disease of the organ, dementia, respiratory problems, hypoglycemia, apnea, lactic acidosis, seizures, swallowing difficulties, developmental delays, movement disorders (dystonia, muscle spasms, tremors, chorea), stroke, and brain atrophy.

Determination of the Biological Effect of the Aromatic-Cationic Peptide-Based Therapeutic.

In various embodiments, suitable in vitro or in vivo assays are performed to determine the effect of a specific aromatic-cationic peptide-based therapeutic and whether its administration is indicated for treatment. In various embodiments, in vitro assays can be performed with representative animal models, to determine if a given aromatic-cationic peptide-based therapeutic exerts the desired effect in reducing disruption of mitochondrial function, such as disruption of OXPHOS. Compounds for use in therapy can be tested in suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects.

Modes of Administration and Effective Dosages

Any method known to those in the art for contacting a cell, organ or tissue with a peptide may be employed. Suitable methods include in vitro, ex vivo, or in vivo methods. In vivo methods typically include the administration of an aromatic-cationic peptide, such as those described above, to a mammal, suitably a human. When used in vivo for therapy, the aromatic-cationic peptides are administered to the subject in effective amounts (i.e., amounts that have desired therapeutic effect). The dose and dosage regimen will depend upon the degree of the infection in the subject, the characteristics of the particular aromatic-cationic peptide used, e.g., its therapeutic index, the subject, and the subject's history.

The effective amount may be determined during preclinical trials and clinical trials by methods familiar to physicians and clinicians. An effective amount of a peptide useful in the methods may be administered to a mammal in need thereof by any of a number of well-known methods for administering pharmaceutical compounds. The peptide may be administered systemically or locally.

The peptide may be formulated as a pharmaceutically acceptable salt. The term "pharmaceutically acceptable salt" means a salt prepared from a base or an acid which is acceptable for administration to a patient, such as a mammal (e.g., salts having acceptable mammalian safety for a given dosage regime). However, it is understood that the salts are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a peptide contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucuronic, mandelic, mucic, nicotinic, orotic, pamoic, pantothenic, sulfonic acids (e.g., benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like. In some embodiments, the salt is an acetate or trifluoroacetate salt.

The aromatic-cationic peptides described herein can be incorporated into pharmaceutical compositions for administration, singly or in combination, to a subject for the treatment or prevention of a disorder or attendant symptoms thereof, described herein. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course (e.g., 7 days of treatment).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The aromatic-cationic peptide compositions can include a carrier, which can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressurized container or dispenser which contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed by iontophoresis.

A therapeutic protein or peptide can be formulated in a carrier system. The carrier can be a colloidal system. The colloidal system can be a liposome, a phospholipid bilayer vehicle. In one embodiment, the therapeutic peptide is encapsulated in a liposome while maintaining peptide integrity. As one skilled in the art would appreciate, there are a variety of methods to prepare liposomes. (See Lichtenberg et al., *Methods Biochem. Anal.*, 33:337-462 (1988); Anselem et al., *Liposome Technology*, CRC Press (1993)). Liposomal formulations can delay clearance and increase cellular uptake (See Reddy, *Ann. Pharmacother.*, 34(7-8):915-923 (2000)). An active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In one embodiment, the therapeutic peptide can be embedded in the polymer matrix, while maintaining protein integrity. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, *Ann. Pharmacother.*, 34(7-8):915-923 (2000)). A polymer formulation for human growth hormone (hGH) has been used in clinical trials. (See Kozarich and Rich, *Chemical Biology*, 2:548-552 (1998)).

Examples of polymer microsphere sustained release formulations are described in PCT publication WO 99/15154 (Tracy et al.), U.S. Pat. Nos. 5,674,534 and 5,716,644 (both to Zale et al.), PCT publication WO 96/40073 (Zale et al.), and PCT publication WO 00/38651 (Shah et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The therapeutic compounds can also be formulated to enhance intracellular delivery. For example, liposomal delivery systems are known in the art, see, e.g., Chonn and Cullis, "Recent Advances in Liposome Drug Delivery Systems," *Current Opinion in Biotechnology* 6:698-708 (1995); Weiner, "Liposomes for Protein Delivery: Selecting Manufacture and Development Processes," *Immunomethods*, 4(3): 201-9 (1994); and Gregoriadis, "Engineering Liposomes for Drug Delivery: Progress and Problems," *Trends Biotechnol.*, 13(12):527-37 (1995). Mizguchi et al., *Cancer Lett.*, 100: 63-69 (1996), describes the use of fusogenic liposomes to deliver a protein to cells both in vivo and in vitro.

Dosage, toxicity and therapeutic efficacy of the therapeutic agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Typically, an effective amount of the aromatic-cationic peptides, sufficient for achieving a therapeutic or prophylactic effect, range from about 0.000001 mg per kilogram body weight per day to about 10,000 mg per kilogram body weight per day. Suitably, the dosage ranges are from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In one embodiment, a single dosage of peptide ranges from 0.001-10,000 micrograms per kg body weight. In one embodiment, aromatic-cationic peptide concentrations in a carrier range from 0.2 to 2000 micrograms per delivered milliliter. An exemplary treatment regime entails administration once per day or once a week. In therapeutic applications, a relatively high dosage at relatively short intervals is sometimes required until progression of the disease is reduced or terminated, and preferably until the subject shows partial or complete amelioration of symptoms of disease. Thereafter, a patient can be administered a prophylactic regime.

In some embodiments, a therapeutically effective amount of an aromatic-cationic peptide may be defined as a concentration of peptide at the target tissue of $10^{-12}$ to $10^{-6}$ molar, e.g., approximately $10^{-7}$ molar. This concentration may be delivered by systemic doses of 0.001 to 100 mg/kg or equivalent dose by body surface area. The schedule of doses would be optimized to maintain the therapeutic concentration at the target tissue, most preferably by single daily or weekly administration, but also including continuous administration (e.g., parenteral infusion or transdermal application).

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The mammal treated in accordance present methods can be any mammal, including, for example, farm animals, such as sheep, pigs, cows, and horses; pet animals, such as dogs and cats; laboratory animals, such as rats, mice and rabbits. In a preferred embodiment, the mammal is a human.

Combination Therapy with an Aromatic-Cationic Peptide and Other Therapeutic Agents In some embodiments, the aromatic-cationic peptides may be combined with one or more additional therapeutic agents for the treatment of mitochondrial diseases or disorders associated with mutations in the SURF1 gene or POLG gene. Treatment for mitochondrial diseases or disorders typically involves taking vitamins and cofactors. In addition, antibiotics, hormones, antineoplastic agents, immunomodulators, dermatologic drugs, antithrombotic, antianemic, and cardiovascular agents, by way of non-limiting example, may also be administered.

In one embodiment, the aromatic-cationic peptide is combined with one or more cofactors or vitamins. By way of example, but not by way of limitation, such compounds may include one or more of CoQ10, Levocarnitine, riboflavin, acetyl-1-carnitine, thiamine, nicotinamide, vitamin E, vitamin C, lipoic acid, selenium, b-carotene, biotin, folic acid, calcium, magnesium, phosphorous, succinate, creatine, uridine, citratesm prednisone, and vitamin K.

In one embodiment, an additional therapeutic agent is administered to a subject in combination with an aromatic cationic peptide, such that a synergistic therapeutic effect is produced. A "synergistic therapeutic effect" refers to a greater-than-additive therapeutic effect which is produced by a combination of two therapeutic agents, and which exceeds that which would otherwise result from individual administration of either therapeutic agent alone. Therefore, lower doses of one or both of the therapeutic agents may be used in treating heart failure, resulting in increased therapeutic efficacy and decreased side-effects.

In any case, the multiple therapeutic agents may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents.

EXAMPLES

The present invention is further illustrated by the following example, which should not be construed as limiting in any way.

Example 1: Confirmation of SURF1 Mutant Subjects

Figure 6:
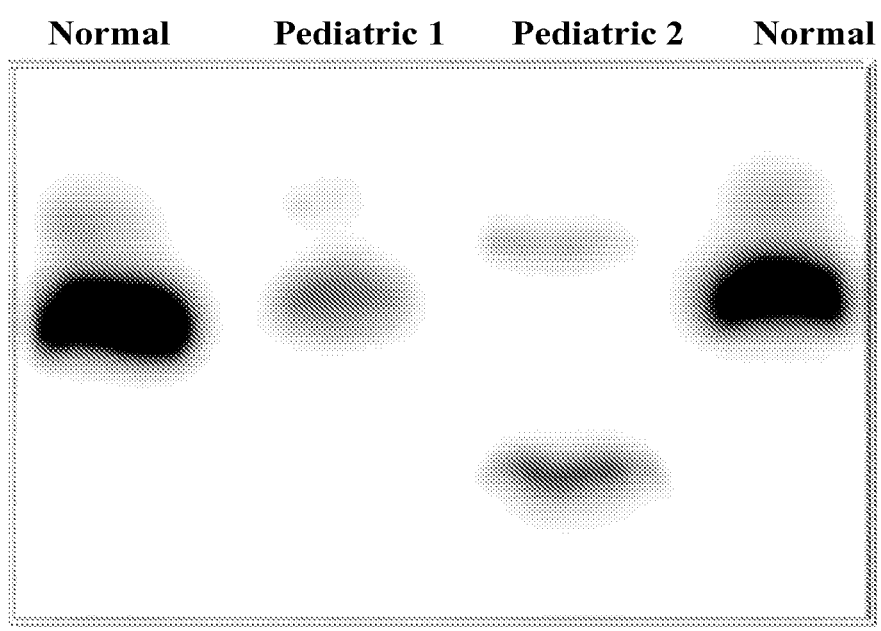
FIG. 6 is an electrophoretic gel illustrating Complex IV monomeric OXPHOS enzyme assembly in subjects with SURF1 mutation.

Mutations of SURF/typically result in profound Complex IV defects. Monomeric Complex IV is highly abnormal showing decreased assembly as well as abnormal high and low molecular weight Complex IV structures (FIG. 1, FIG. 6). FIG. 1 shows the monomeric Complex IV from a pediatric patient and adult patient with Leigh disease. The pediatric patient shows decreased monomeric Complex IV assembly with an abnormal molecular weight form of Complex IV. These abnormal Complex IV structures likely represent abnormally assembled and dysfunctional Complex IV. FIG. 6 shows complex IV assembly in two pediatric subjects with Leigh disease. Accordingly, subjects suffering from Leigh disease could be treated with the aromatic-cationic peptides disclosed herein.

Example 2: D-Arg-2',6'-Dmt-Lys-Phe-NH$_2$(SS-31) Increases OXPHOS in SURF1 Mutations SURF1 was mutated in two regions: 1) exon 4: 344-353 del 10, ins AT (deleted sequence=TCTGCCAGCC)(heterozygous) and 2) exon 9: 875-876 del CT (heterozygous). Fibroblast cells were transformed with mutated SURF b 1.

The mutated SURF1 transformed cells were then grown in DMEM and split into three groups. Group 1, the saline group, was treated with DMEM+saline. Group 2, the chronic treatment group, was treated with DMEM+10 nM SS-31 for 5 days. Group 3, the acute treatment group, was treated with DMEM+10 nM SS-31 for 1 day (16-24 hours). Untransformed fibroblasts cells were used as controls and were divided into 3 treatment groups as listed above.

Transformed and control fibroblasts were also cultured in glycolysis inhibited conditions. In the glycolysis inhibited condition, fibroblasts were cultured in glycolysis inhibition media supplemented with lactate and pyruvate. The glycolysis inhibition conditions increased the dependence of the cells on oxidative phosphorylation and made changes more apparent.

Uncoupling ratio (UCR) is an expression of the respiratory reserve capacity and indicates the OXPHOS capacity of the cells. UCR is defined as $Cr_u/Cr$. $Cr_u$ is the maximum rate of oxygen utilization (Oxygen flux) produced when mitochondria are chemically uncoupled using FCCP (Carbonyl cyanide 4-(trifluoromethoxy) phenylhydrazone). FCCP titration must be performed since the concentration of FCCP required to produce maximum oxygen utilization varies among different cell lines. Once the maximum oxygen utilization is reached, further increases in FCCP inhibit oxygen utilization by oxidative phosphorylation. Cr represents oxygen utilization by the cells during a normal cellular respiration with excess substrates. The following additional assays were performed and the following definitions are used:
1) Uncoupling ratio (UCR): The UCR is defined as Cm/Cr. The UCR is an expression of the respiratory reserve capacity. Cm is the maximum rate of oxygen utilization (Oxygen flux) produced when mitochondria are chemically uncoupled using FCCP (Carbonyl cyanide 4-(trifluoromethoxy) phenylhydrazone). FCCP titration must be performed since the concentration of FCCP required to produce maximum oxygen utilization varies among different cell lines. Once the maximum oxygen utilization is reached, further increases in FCCP inhibit oxygen utilization by oxidative phosphorylation (OXPHOS). Cr represents oxygen utilization by the cells during a normal cellular respiration with excess substrates.
2) Net Routine Flux Control Ratio (Cr/Cm). This value is the inverse of the UCR. This value assesses how close routine respiration operate to the respiratory capacity of oxidative phosphorylation.
3) Respiratory Control Ratio (RCR): The RCR is defined as Cm/Cro. Cm is defined above. Cro=Respiration after inhibition of Complex V (ATP synthase) by oligomycin. This ratio allows assessment of uncoupling and OXPHOS dysfunction.
4) Leak Flux Control Ratio: Cro/Cru. This parameter is the inverse of RCR and represent proton leak with inhibition of ADP phosphorylation by oligomycin.
5) Phosphorylation Respiratory Control Ratio: The RCRp is defined as (Cr−Cro)/Cru (or 1/UCR−1/RCR). The RCRp is an index which expresses phosphorylation-related respiration (Cr−Cro) as a function of respiratory capacity (Cm). The RCRp remains constant, if partial uncoupling is fully compensated by an increased routine respiration rate and a constant rate of oxidative phosphorylation is maintained. If the respiratory capacity declines without effect on the rate of oxidative phorphorylation, however, the RCRp increases, which indicates that a higher proportion of the maximum capacity is activated to drive ATP synthesis. The RCRp declines to zero in either fully uncoupled cells or in cells under complete metabolic arrest.

Results are shown in FIG. 2A-G. "Stealth 2" in the Figures is the name of the fibroblast cell line carrying the SURF1 mutant; "Stealth 4" in the Figures is the name of the fibroblast cell line carrying the POLG mutant. As shown in the figures, the aromatic-cationic peptides of the present disclosure are useful to treat mitochondrial disorders, such as those caused by SURF 1 mutations, e.g., Leigh syndrome, and to treat diseases or conditions associated with deregulation of OXPHOS.

Example 3: D-Arg-2',6'-Dmt-Lys-Phe-NH$_2$ Increases OXPHOS in POLG Mutations

Fibroblast cells were transformed with a POLG mutated gene, mutation at exon 7; c.13399G>A, p. Ala467Thr (homozygous). POLG encodes the catalytic subunit of DNA polymerase gamma, which is required for replication and repair of the mitochondrial DNA. Mutations in POLG are known to cause progressive external ophthalmoplegia (PEO), Alpers' disease, and sensory ataxic neuropathy with dysarthria and ophthalmoparesis (SANDO).

The mutated POLG fibroblast cells were grown and split into three groups. Group 1, the saline group, was treated with DMEM and saline. Group 2, the chronic treatment group, was treated with DMEM+10 nM D-Arg-2',6'-Dmt-Lys-Phe-NH$_2$ for 5 days. Group 3, the acute treatment group, was treated with DMEM+10 nM D-Arg-2',6'-Dmt-Lys-Phe-NH$_2$ for 1 day (16-24 hours). Untransformed fibroblasts cells were used as controls and were divided into 3 treatment groups as listed above.

Transformed and control fibroblasts were also cultured in glycolysis inhibited conditions. In the glycolysis inhibited condition, fibroblasts were cultured in glycolysis inhibition media supplemented with lactate and pyruvate. The glycolysis inhibition conditions increased the dependence of the cells on oxidative phosphorylation and made changes more apparent. The following definitions are used:

Effects of D-Arg-2',6'-Dmt-Lys-Phe-NH$_2$ treatment was measured by UCR. Uncoupling ratio (UCR) is an expression of the respiratory reserve capacity and indicates the OXPHOS capacity of the cells. UCR is defined as $Cr_u$/Cr. $Cr_u$ is the maximum rate of oxygen utilization (Oxygen flux) produced when mitochondria are chemically uncoupled using FCCP (Carbonyl cyanide 4-(trifluoromethoxy) phenylhydrazone). FCCP titration must be performed since the concentration of FCCP required to produce maximum oxygen utilization varies among different cell lines. Once the maximum oxygen utilization is reached, further increases in FCCP inhibit oxygen utilization by oxidative phosphorylation. Cr represents oxygen utilization by the cells during a normal cellular respiration with excess substrates. The following additional assays were performed and the following definitions are used:
1) Uncoupling ratio (UCR): The UCR is defined as Cm/Cr. The UCR is an expression of the respiratory reserve capacity. Cm is the maximum rate of oxygen utilization (Oxygen flux) produced when mitochondria are chemically uncoupled using FCCP (Carbonyl cyanide 4-(trifluoromethoxy) phenylhydrazone). FCCP titration must be performed since the concentration of FCCP required to produce maximum oxygen utilization varies among different cell lines. Once the maximum oxygen utilization is reached, further increases in FCCP inhibit oxygen utilization by oxidative phosphorylation (OXPHOS). Cr represents oxygen utilization by the cells during a normal cellular respiration with excess substrates.
2) Net Routine Flux Control Ratio (Cr/Cm). This value is the inverse of the UCR. This value assesses how close routine respiration operate to the respiratory capacity of oxidative phosphorylation.
3) Respiratory Control Ratio (RCR): The RCR is defined as Cm/Cro. Cm is defined above. Cro=Respiration after inhibition of Complex V (ATP synthase) by oligomycin. This ratio allows assessment of uncoupling and OXPHOS dysfunction.
4) Leak Flux Control Ratio: Cro/Cm. This parameter is the inverse of RCR and represent proton leak with inhibition of ADP phosphorylation by oligomycin.
5) Phosphorylation Respiratory Control Ratio: The RCRp is defined as (Cr−Cro)/Cru (or 1/UCR−1/RCR). The RCRp is an index which expresses phosphorylation-related respiration (Cr−Cro) as a function of respiratory capacity (Cm). The RCRp remains constant, if partial uncoupling is fully compensated by an increased routine respiration rate and a constant rate of oxidative phosphorylation is maintained. If the respiratory capacity declines without effect on the rate of oxidative phorphorylation, however, the RCRp increases, which indicates that a higher proportion of the maximum capacity is activated to drive ATP synthesis. The RCRp declines to zero in either fully uncoupled cells or in cells under complete metabolic arrest.

Results are shown in FIG. 3A-G. "Stealth 4" in the Figures is the name of the fibroblast cell line carrying the POLG mutant. As shown in the figures, the aromatic-cationic peptides of the present disclosure, such as D-Arg-2',6'-Dmt-Lys-Phe-NH$_2$, or a pharmaceutically acceptable salt thereof, are useful to treat mitochondrial disorders, such as those caused by POLG mutations, e.g., Alper's Disease, progressive external ophthalmoplegia (PEO), and sensory ataxic neuropathy with dysarthria and ophthalmoparesis (SANDO), and to treat diseases or conditions associated with deregulation of OXPHOS.

EQUIVALENTS

The present invention is not to be limited in terms of the particular embodiments described in this application, which are intended as single illustrations of individual aspects of the invention. Many modifications and variations of this invention can be made without departing from its spirit and scope, as were apparent to those skilled in the art. Functionally equivalent methods and apparatuses within the scope of the invention, in addition to those enumerated herein, were apparent to those skilled in the art from the foregoing descriptions. Such modifications and variations are intended to fall within the scope of the appended claims. The present invention is to be limited only by the terms of the appended claims, along with the full scope of equivalents to which such claims are entitled. It is to be understood that this invention is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As were understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as were understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

What is claimed is:

1. A method for ameliorating a disease selected from the group consisting of Leigh syndrome, Alpers' disease, ataxia-neuropathy disorders, and progressive external ophthalmoplegia in a subject in need thereof, the method comprising: administering to the subject a therapeutically effective amount of the peptide D-Arg-2',6'-Dmt-Lys-Phe-NH2 or a pharmaceutically acceptable salt thereof, wherein the Leigh syndrome is associated with a loss-of-function mutation in the SURF 1 gene resulting in a disruption of mitochondrial oxidative phosphorylation due to impairment of the complete assembly of at least one mitochondrial complex selected from the group consisting of Complex I; Complex II; Complex III; Complex IV, and the Alpers' disease, ataxia-neuropathy disorders, and progressive external ophthalmoplegia are associated with a loss-of-function mutation in the POLG gene resulting in a disruption of mitochondrial oxidative phosphorylation.

2. The method of claim 1, wherein the peptide is administered orally, topically, systematically, intravenously, subcutaneously, intraperitoneally, or intramuscularly.

3. The method of claim 1, wherein the disease is Leigh syndrome associated with a loss-of-function mutation in the SURF 1 gene resulting in a disruption of mitochondrial oxidative phosphorylation due to impairment of the complete assembly of at least one mitochondrial complex selected from the group consisting of Complex I; Complex II; Complex III; Complex IV.

4. The method of claim 1, wherein the disease is Alpers' disease associated with a loss-of-function mutation in the POLG gene resulting in a disruption of mitochondrial oxidative phosphorylation.

5. The method of claim 1, wherein the disease is ataxia-neuropathy disorders associated with a loss-of-function mutation in the POLG gene resulting in a disruption of mitochondrial oxidative phosphorylation.

6. The method of claim 1, wherein the disease is progressive external ophthalmoplegia associated with a loss-of-function mutation in the POLG gene resulting in a disruption of mitochondrial oxidative phosphorylation.

* * * * *